(12) United States Patent
Schoch et al.

(10) Patent No.: US 11,678,791 B2
(45) Date of Patent: Jun. 20, 2023

(54) IMAGING SYSTEM AND OBSERVATION METHOD

(71) Applicant: KARL STORZ SE & CO. KG, Tuttlingen (DE)

(72) Inventors: Dieter Schoch, Tuttlingen (DE); Marius Zepf, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 336 days.

(21) Appl. No.: 16/891,573

(22) Filed: Jun. 3, 2020

(65) Prior Publication Data
US 2020/0380718 A1  Dec. 3, 2020

(30) Foreign Application Priority Data
Jun. 3, 2019  (DE) ................ 10 2019 114 817.0

(51) Int. Cl.
*A61B 1/00* (2006.01)
*G06T 7/73* (2017.01)
(Continued)

(52) U.S. Cl.
CPC ...... *A61B 1/00193* (2013.01); *A61B 1/00006* (2013.01); *A61B 1/00009* (2013.01);
(Continued)

(58) Field of Classification Search
CPC ... G06T 7/73; A61B 1/00006; A61B 1/00193; A61B 1/00009; A61B 1/00045;
(Continued)

(56) References Cited

U.S. PATENT DOCUMENTS 5,359,712 A  10/1994  Cohen et al.
5,496,261 A   3/1996  Sander
(Continued)

FOREIGN PATENT DOCUMENTS

DE        19613431 A1   10/1996
DE     102004059143 A1    6/2006
(Continued)

OTHER PUBLICATIONS

Notification of Reasons for Rejection (Including Translation) for corresponding Japanese Patent Application No. 2020-093928, dated Jun. 8, 2021.
(Continued)

*Primary Examiner* — Tracy Y. Li
(74) *Attorney, Agent, or Firm* — Jason H. Vick; Sheridan Ross, PC

(57) ABSTRACT

A stereo imaging system comprises an observation instrument having an image acquisition unit for detecting first image data and second image data, which can be combined for stereo observation. There is provided at least one position sensor for detecting an orientation of the instrument in relation to a position reference. There is provided a control device that is operable in a first representation mode and a second representation mode, depending on the orientation of the instrument. The control device is configured for outputting an image signal, which comprises a stereo signal that is based on the first image data and the second image data in the first representation mode, and a mono signal that is based on the first image data or the second image data in the second representation mode. The control device is configured to erect images that are output with the image signal in the second representation mode, depending on the orientation.

21 Claims, 9 Drawing Sheets

(51) Int. Cl.
*H04N 23/00* (2023.01)
*H04N 23/50* (2023.01)

(52) U.S. Cl.
CPC ............ *A61B 1/00194* (2022.02); *G06T 7/73* (2017.01); *H04N 23/00* (2023.01); *H04N 23/555* (2023.01)

(58) Field of Classification Search
CPC ............ A61B 1/00066; A61B 1/00071; A61B 1/00177; A61B 1/00179; A61B 1/00194; A61B 1/045; A61B 1/00064; A61B 1/00131; A61B 1/04; A61B 1/05; A61B 2503/40; H04N 5/225; H04N 2005/2255; H04N 13/239; H04N 13/286; H04N 13/296; H04N 13/20; G02B 23/2415; G02B 23/2484
See application file for complete search history.

(56) References Cited

U.S. PATENT DOCUMENTS

| | | | |
|---|---|---|---|
| 5,545,120 | A | 8/1996 | Chen |
| 6,191,809 | B1 | 2/2001 | Hori et al. |
| 6,522,906 | B1 | 2/2003 | Salisbury, Jr. et al. |
| 6,799,065 | B1 | 9/2004 | Niemeyer |
| 7,037,258 | B2 | 5/2006 | Chatenever et al. |
| 7,108,657 | B2 | 9/2006 | Irion et al. |
| 7,134,992 | B2 | 11/2006 | Schara et al. |
| 9,848,758 | B2 | 12/2017 | Ushijima |
| 10,122,897 | B2 | 11/2018 | Heni et al. |
| 2008/0303899 | A1 | 12/2008 | Berci |
| 2009/0088634 | A1* | 4/2009 | Zhao ............. B25J 9/1656 600/425 |
| 2009/0207241 | A1 | 8/2009 | Igarashi et al. |
| 2011/0276058 | A1 | 11/2011 | Choi et al. |
| 2012/0289858 | A1 | 11/2012 | Ouyang et al. |
| 2013/0038689 | A1 | 2/2013 | McDowall |
| 2014/0323801 | A1 | 10/2014 | Konno et al. |
| 2016/0335755 | A1* | 11/2016 | Hilsebecher ......... H04N 13/246 |
| 2017/0143442 | A1* | 5/2017 | Tesar ................... A61B 90/37 |
| 2017/0150138 | A1* | 5/2017 | Kosmiskas .......... H04N 13/398 |
| 2017/0188792 | A1 | 7/2017 | Itkowitz et al. |
| 2018/0042453 | A1 | 2/2018 | Hino |
| 2019/0090728 | A1 | 3/2019 | Fanebruck et al. |

FOREIGN PATENT DOCUMENTS

| | | |
|---|---|---|
| DE | 102010041870 A1 | 4/2012 |
| DE | 102017219621 A1 | 3/2019 |
| EP | 1925962 A1 | 5/2008 |
| EP | 2424253 A2 | 2/2012 |
| EP | 2441410 A1 | 4/2012 |
| JP | H06-269406 A | 9/1994 |
| JP | H10-192233 A | 7/1998 |
| JP | 2001-145640 A | 5/2001 |
| JP | 2010-206495 A | 9/2010 |
| KR | 10-1500717 B1 | 3/2015 |
| WO | WO 01/35848 | 5/2001 |
| WO | WO 2010/105946 | 9/2010 |
| WO | WO 2012/001549 | 1/2012 |
| WO | WO 2016/012248 | 1/2016 |

OTHER PUBLICATIONS

Higuchi, Ty T. et al. "Chapter 2—Robotic Instrumentation, Personnel and Operating Room Setup" L.-M. Su, Atlas of Robotic Urologic Surgery, 2011, pp. 15-30.
Moll, A. et al. "Unrotating Images in Laparoscopy with an Application for 30° Laparoscopes" ECIFMBE 2008, IFMBE Proceedings 22, pp. 966-969, 2008.
Warren, Alexander et al. "Horizon Stabilized—Dynamic View Expansion for Robotic Assisted Surgery (HS-DVE)" International Journal of Computer Assisted Radiology and Surgery; Jun. 2011.
German Search Report for German Patent Application No. 10201911481.0, dated Feb. 12. 2020.
European Search Report for European Application No. 20177131.8, dated Sep. 23, 2020.

* cited by examiner

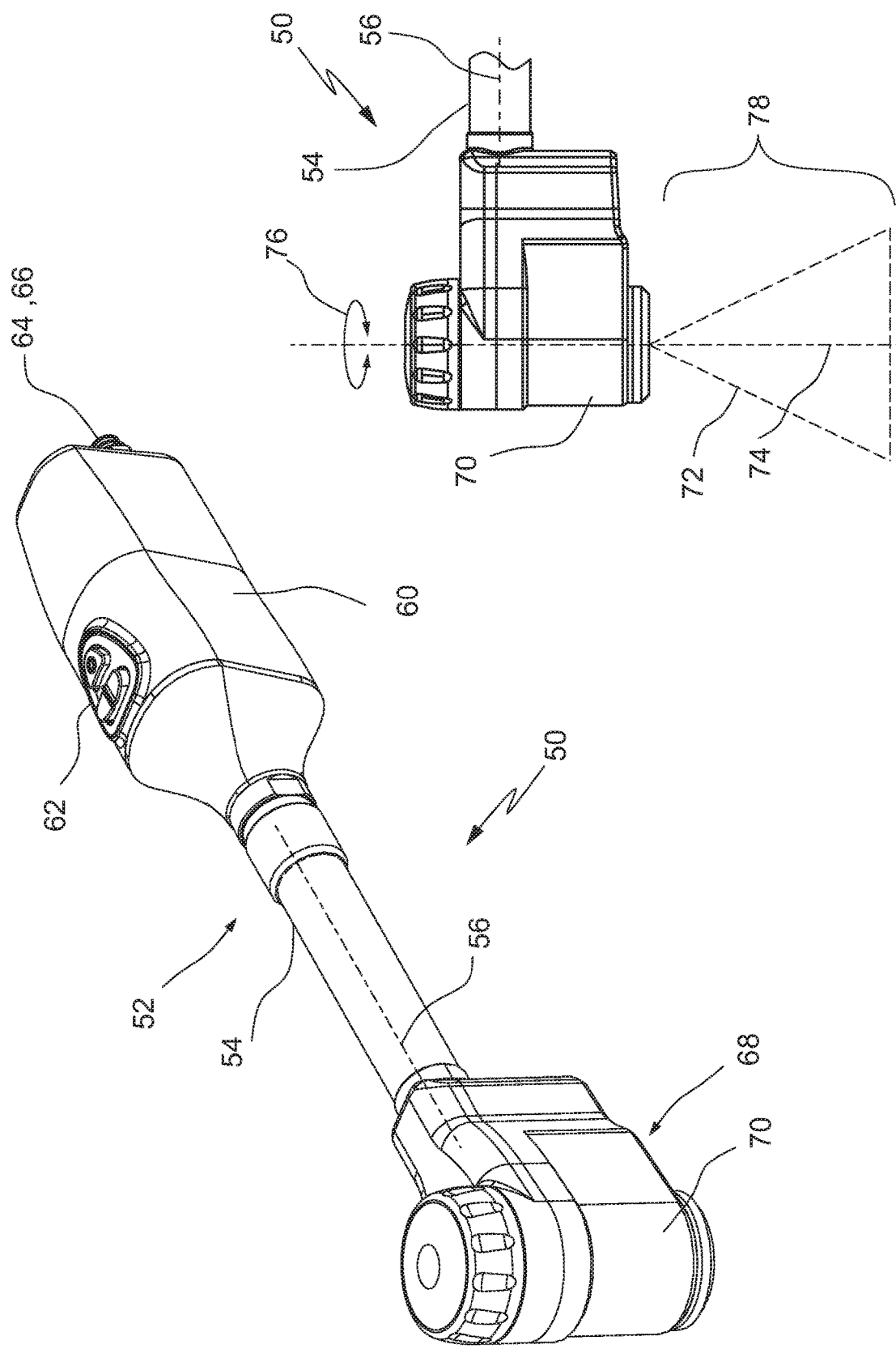

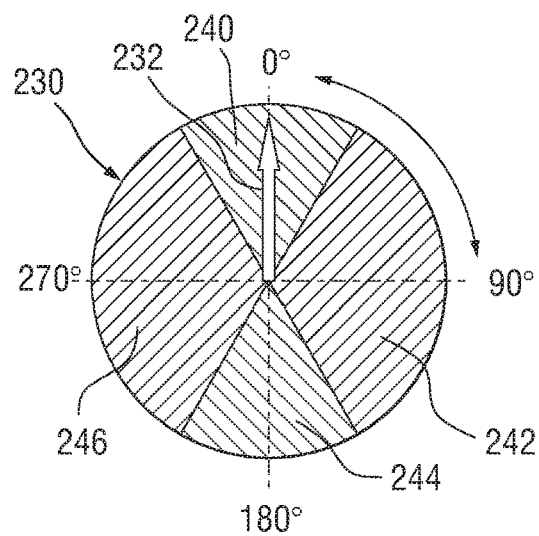
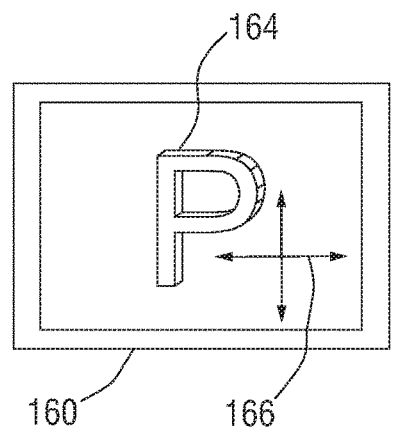
Fig.9
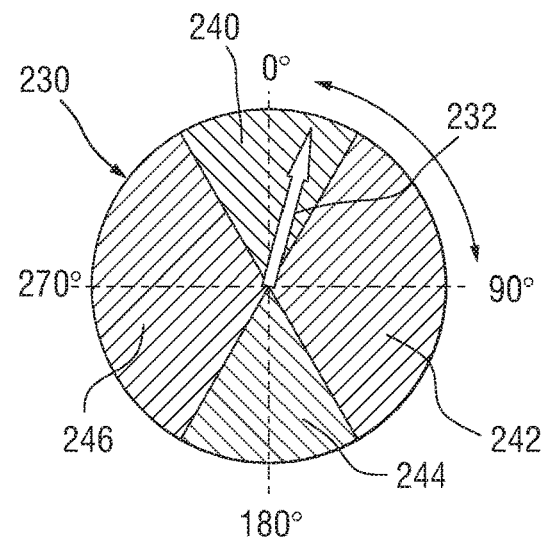
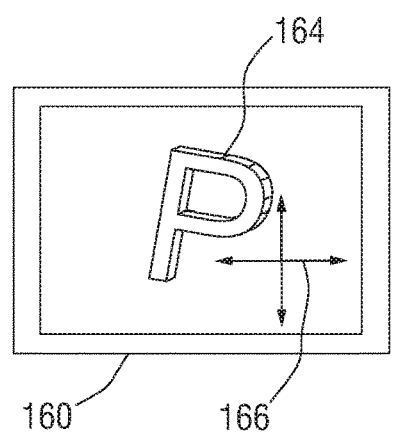
Fig.10
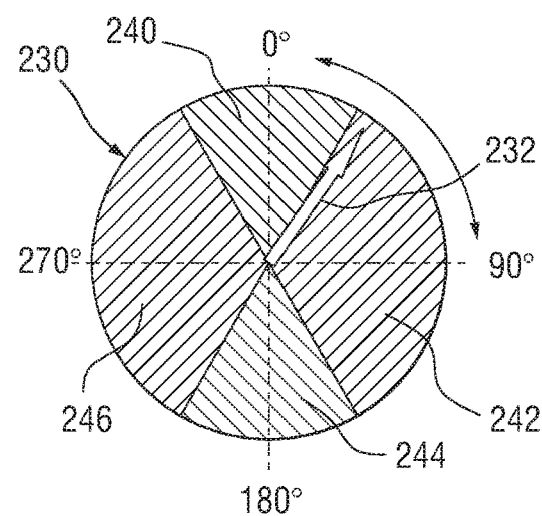
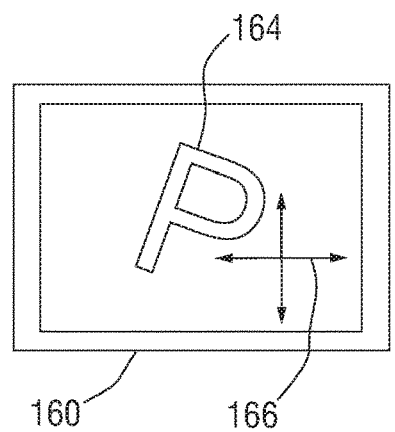
Fig.11

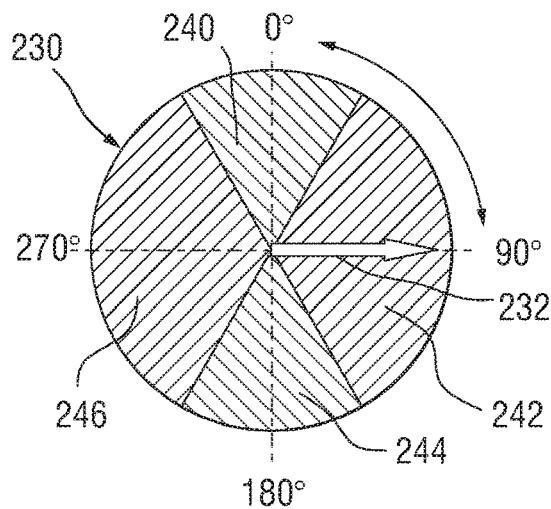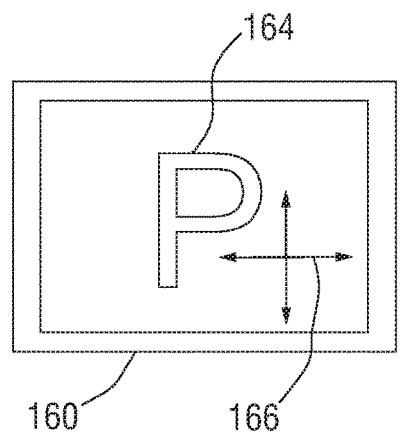
Fig.12
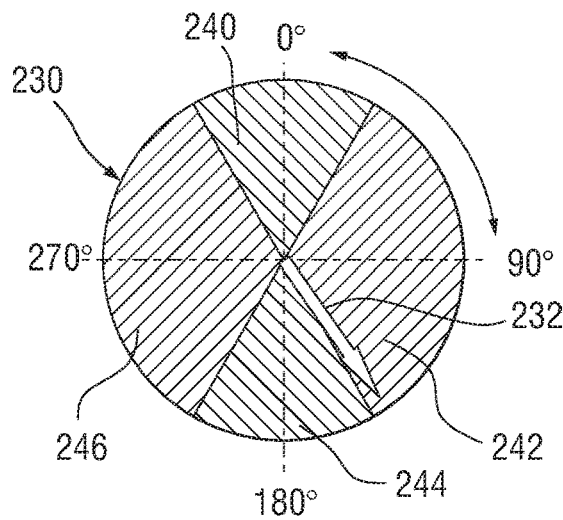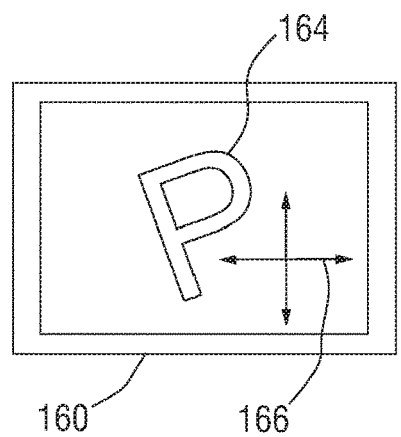
Fig.13
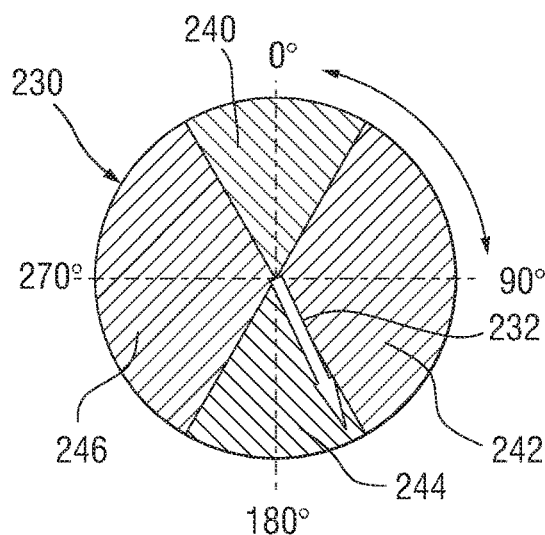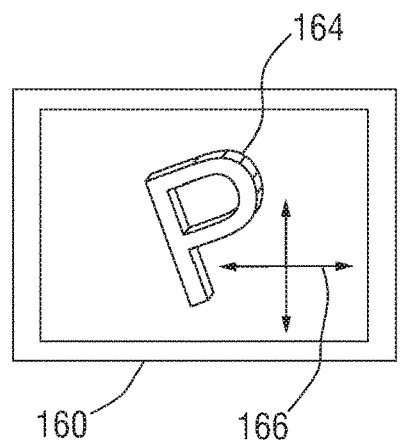
Fig.14

IMAGING SYSTEM AND OBSERVATION METHOD

CROSS REFERENCE TO RELATED APPLICATIONS

This application claims priority from German patent application 10 2019 114 817.0, filed on Jun. 3, 2019. The entire content of that priority application is incorporated herein by reference.

BACKGROUND

In some embodiments, the present disclosure relates to a stereo imaging system comprising an observation instrument having an image acquisition unit for detecting first image data and second image data, which can be combined for stereo observation.

In certain embodiments, the present disclosure relates to a medical imaging system. Such imaging systems are frequently used to observe the human and/or animal body.

Imaging systems that are suitable for stereo observation usually comprise observation instruments having stereoscopic observation optics and stereo image sensors, e.g. two image sensors that are offset to each other. There are therefore two observation channels, at least in certain arrangements. Image sensors may involve CCD sensors, CMOS sensors and the like. When using two image sensors that are offset to each other, one of the two image sensors is assigned to the right eye (first observation channel) and the other one of the two image sensors to the left eye of the observer (second observation channel).

Imaging systems that are suitable for stereo observation are occasionally also referred to as 3D imaging systems. It is understood that with these systems 3D data is not necessarily captured. However, the 3D image generated in this way allows the observer to perceive depth information.

Medical imaging systems include systems for endoscopic observation, for instance. For the purposes of the present disclosure, endoscopic imaging systems include designs, in which a probe-like instrument is arranged to be inserted into natural or artificially created body orifices to acquire images of the interior of the body. This also includes so-called video endoscopy systems.

From U.S. Pat. No. 9,848,758 B2 there is known an instrument that is arranged as a stereo endoscope, in which image data for the right and left channel is corrected, and in which identification information is obtained, based on a test during the assembly of the endoscope, to ensure that the correction data is actually provided for the right and the left channel, respectively.

From WO 2010/105946 A1 there is known an endoscope, comprising an image sensor and an inertial sensor at the distal end, wherein the inertial sensor is configured for detecting a tilting of the image sensor relative to the gravitational field, wherein the endoscope further comprises a control device, wherein the image sensor comprises an array of image pixels, to generate image data, wherein the inertial sensor is adapted to generate a tilt signal representing the tilting, and wherein the control device is adapted to combine the tilt signal with the image data into a combination signal by replacing a portion of the image data with the tilt signal.

From US 2019/0090728 A1 there is known a medical visualization system, comprising an endoscope and a microscope, which are positioned in different orientations and whose visual axes can be inclined to each other. The endoscope is provided with a motion sensor, wherein an angle of the visual axis of the endoscope relative to the visual axis of the microscope is detected. A display device is provided, which displays a first image based on the microscope data and a second image based on the endoscope data, wherein the orientation of the second image can be oriented dependent on the angle of the visual axis of the endoscope.

From WO 2016/012248 A1 there is known a stereo endoscope with distally arranged image sensors. Embodiments with straight direction of view and embodiments with inclined direction of view are described.

From U.S. Pat. No. 7,108,657 B2 there is known an endoscopic visualization device, comprising two image sensors, which are offset from each other, wherein it is proposed to make the two image sensors each rotatable about an axis that is perpendicular to their sensor plane. In this way, the captured image can be rotated. Thus, an image erection function is provided.

From the U.S. Pat. No. 7,037,258 B2 there is known a video endoscope, comprising means for image erection is known. The endoscope is designed as a monoscopic instrument. It is therefore an instrument with one observation channel. The image is electronically rotated and erected, respectively.

From U.S. Pat. No. 7,134,992 B2 there is known another video endoscope, comprising means for image erection. It is proposed to erect the captured image depending on a determined orientation of the instrument. The endoscope comprises an image sensor located at the distal end. It is a monoscopic observation instrument with one observation channel. Acceleration sensors are used to detect the orientation.

Furthermore, in certain embodiments, the present disclosure relates to medical imaging systems that are arranged for observing the body from outside the body. In other words, with these systems it is not intended to insert the instrument at least partially into a body orifice. Such systems, and in particular their observation instruments, are referred to as exoscopes, for instance. Such an exoscope having stereoscopic optics is known from U.S. Pat. No. 10,122,897 B2. It is proposed therein to make the optical unit rotatable in order to erect the image of the instrument, if necessary. In this way, the orientation of the stereo base of the stereoscopic optics may be adapted so that stereoscopic observation is possible even when the orientation and/or position of the instrument changes.

At least in exemplary embodiments, the present disclosure relates to imaging systems and instruments for white light observation. This includes the detection of visible light, in particular of portions of the electromagnetic spectrum that are visible to the human eye. This involves, for example, a range from 380 nm to 750 nm (nanometers). However, this is not to be understood to be limiting.

In certain embodiments, however, this does not preclude the possibility that an imaging system in accordance with the present disclosure may also be capable of acquiring image information for observation in the infrared or near-infrared range and/or in the ultraviolet range. This is conceivable, for example, with instruments for PDD (photodynamic diagnostics) and/or PDT (photodynamic therapy) as well as for instruments for fluorescence observation.

However, at least in certain embodiments, this should not include radiological imaging methods (e.g. radiography, computed tomography, magnetic resonance imaging, ultrasound observation). Accordingly, the focus of the present disclosure is not on imaging systems for slice image observation. However, essential aspects of the present disclosure refer to the observation of surfaces or objects close to surfaces. It is understood that combined imaging systems are nevertheless conceivable.

When using observation instruments of the aforementioned type, it is often necessary to rotate or otherwise move them, for example around their longitudinal axis (axis of the instrument shaft or observation optics), in order to change the observed image section. This may be the case with hand-held and/or hand-guided instruments, in certain embodiments. However, even with instruments that are rigidly mounted, degrees of freedom of movement may be provided to position the instrument and its observation optics in the desired way.

For observation instruments with only one image sensor, the orientation of the image sensor in relation to a reference horizon (defined by a display device, for example a monitor) can be adjusted by rotating the image mechanically or electronically. In this way, an image erection can be performed. For the purposes of the present disclosure, image erection is understood to be a functionality by means of which the orientation (such as the directions up, down, right, left) of the displayed image is largely or completely retained, even though the image sensor and/or observation optics are rotated (in terms of a rolling motion). This definition may also be applied analogously to observation instruments with inclined direction of view, e.g. to instruments with lenses whose "normal" is not parallel to the axis of rotation. In the case of an objective, the "normal" is for instance the optical axis. For example, in the case of an image sensor that is concentric to the lens, the "normal" is for instance perpendicular to the sensor plane. Normally, the optical axis of the lens is essential for defining the direction of view.

However, it is also conceivable not to erect the image, so that the displayed image rotates with the rotation or rolling of the instrument. Corresponding representation modes can be optionally selected.

With an instrument designed for stereo observation, image erection poses various challenges. The main reason for this is the so-called stereo base, i.e. an offset (distance and/or angle) between the two observation channels and/or image sensors that are combined for stereo observation and stereo representation. The stereo base is ideally aligned with the reference horizon of the display device, ideally parallel or nearly parallel thereto. The reference horizon of the display device usually corresponds to a horizontal. An observer with a straight-ahead head aligns his eyes (imaginary line through the two eyes) parallel thereto. This is not to be understood to be limiting.

A general design goal for imaging systems in medical or industrial environments is to keep the probe part small. This may also include miniaturization of the image acquisition unit. This applies, for example, to a diameter of the probe and/or lens assembly. This design goal is all the more important for endoscopic instruments used in neurosurgery (brain surgery, spine surgery, etc.). However, this makes mechanical solutions for image erection even more difficult.

In general, it is desirable to design shaft assemblies of endoscopic instruments with the shaft diameter as small as possible. This can minimize trauma to the patient when creating the access opening. Therefore, this design goal applies generally to instruments for minimally invasive surgery, at least in certain embodiments.

Nevertheless, there is a need for stereoscopic image acquisition and/or observation also with instruments that are as small as possible (in terms of shaft diameter). One approach for a stereoscopic instrument, such as an endoscope, may be to place two image sensors at or near the distal end of the instrument. The two image sensors are regularly placed next to each other and therefore affect the overall diameter of the instrument in that area. In this area, it would be very costly to provide additional provisions for mechanical image erection, at least in certain embodiments.

Nevertheless, even such instruments are often rotated around the longitudinal axis of the shaft during use. This is may be the case for instruments with an inclined viewing direction, in certain embodiments. As already mentioned above, however, this poses challenges for stereoscopic perception, at least if the image is to remain upright even during a rolling movement. If, conversely, the upright position is not maintained, the orientation "in the image" is made more difficult for the observer.

Instruments with only one image sensor, i.e. with only one observation channel (monoscopic instruments) are less problematic in this respect. The captured image can be erected mechanically (actually by hand or via an actuator) or electronically (digital image erection). The mechanical erection involves a rotation of the sensor in relation to the shaft and/or a mounting piece of the instrument. The electronic image erection includes image processing measures to ensure that the image is reproduced upright, if necessary.

In view of this, it is an object of the present disclosure to present a stereo imaging system that addresses at least some of the afore-mentioned challenges.

It is another object of the present disclosure to present a stereo imaging system comprising an observation instrument, which enables a clearly perceptible representation even in case of a rotation of the instrument or the image acquisition unit of the instrument.

It is a further object of the present disclosure to present an imaging system, wherein the reproduced image can be erected, if needed and appropriate, at least in certain embodiments.

It is a further object of the present disclosure to present an imaging system, which, nevertheless, enables stereoscopic (or 3D) representation in a rotation range that is as large as possible, at least in certain embodiments.

It is a further object of the present disclosure to present an imaging system, which is easy and intuitively operable, at least in certain embodiments.

It is a further object of the present disclosure to present an imaging system, which still provides a certain basic functionality in a state, in which stereoscopic detecting and representation is not useful, so that at least one observation channel can be used.

It is yet a further object of the present disclosure to present a corresponding method for stereo observation.

In certain embodiments, the present disclosure also relates to a corresponding computer program for controlling a stereo imaging system, and to a corresponding non-transitory computer-readable storage medium.

SUMMARY

In regard of the imaging system, these and other objects are achieved by a stereo imaging system, such as a medical stereo imaging system, the imaging system comprising:
- an observation instrument comprising an image acquisition unit for detecting first image data and second image data, which can be combined for stereo observation,
- at least one position sensor for detecting an orientation, for instance a rotation orientation, of the instrument in relation to a position reference, a control device that is operable in a first representation mode and a second representation mode depending on the orientation of the instrument, wherein the control device is configured for outputting an image signal, which in the first representation mode comprises a stereo signal based on the first image data and the second image data, and in the second representation mode comprises a mono signal based on the first image data or the second image data, and wherein the control device is configured to erect images that are output with the image signal in the second representation mode depending on the orientation.

In this way, in accordance with certain embodiments, on the one hand, the ability for stereo observation is used. This applies in any case in such positions (for instance rotation positions) of the image acquisition unit, in which the orientation of the stereo base does not deviate from the position reference (e.g. from the horizon and/or artificial horizon) or only deviates within reasonable limits.

However, if the signals provided by the position sensor with respect to the orientation (rotation position and/or roll position) indicate that the stereo functionality is no longer usable due to the rotation of the image acquisition unit, the control device can output a mono signal (using only one observation channel). This may be the case when the operator can no longer orientate himself well in the image, for example when controlling surgical instruments that are visible there, at least in certain embodiments.

In certain embodiments, the above-mentioned measures may enable image erection, for instance an electronic image erection. Depending on the current rotation angle, a stereoscopic representation based on two observation channels or a monoscopic representation based on one observation channel is possible, at least in certain embodiments.

In certain embodiments, this means indeed that in certain orientations of the observation instrument and/or its image acquisition unit only a two-dimensional representation without depth impression is used. Nevertheless, this type of representation may also be used for observation.

However, in certain embodiments, if the position sensor determines that the current rotation orientation (roll position) of the image acquisition unit allows stereoscopic reproduction, i.e. a representation with depth impression (3D reproduction), then it is possible to switch to stereoscopic representation. With regard to image erection, it is conceivable that if the image acquisition unit is rotated by about 180°, the two observation channels for the representation are swap and their image information is rotated by 180° each. In this way, an image erection may also be possible with stereoscopic representation, at least for a small rotation angle range (at about 180°).

In certain embodiments, according to this approach, an instrument may be provided, at least in exemplary embodiments, in which on the one hand stereo observation and on the other hand electronic image erection is possible. This relates to exemplary embodiments and is not to be understood to be limiting.

Nevertheless, in certain embodiments, this approach is suitable for instruments having a small shaft diameter, i.e. for instruments for minimally invasive surgery, especially for neurosurgery (brain surgery, spinal surgery), at least in certain embodiments. In exemplary embodiments, the observation instrument is a medical observation instrument. The smaller the shaft diameter, the more difficult it is to implement mechanical solutions for image erection.

In certain embodiments, the observation instrument is generally arranged as a video endoscope or video exoscope.

A video endoscope is configured for observing the inside of the body and can be inserted into the body through a natural or artificial body orifice. A video exoscope is configured for observing the body from outside the body. The instruments may be designed for human medicine and, if necessary, for veterinary medicine. This is not to be understood to be limiting. Nevertheless, industrial applications for video endoscopes and video exoscopes are also conceivable.

In certain embodiments, the position reference, to which the position signal determined by the position sensor refers, can be a horizon (possibly an artificial horizon), for instance. The position reference results, for example, from the inter-pupillary distance (and/or the orientation of the corresponding vector) of the observer when viewing the reproduced image.

In certain embodiments, for example, the image acquisition unit comprises two image sensors that are spaced apart from each other. These can be parallel to each other but also slightly inclined relative to each other. Each of the two image sensors (right and left) is assigned one of two observation channels. The two image sensors can be combined for stereo observation of an object in one object plane. The two image sensors are spaced apart from each other and accordingly adapted to the disparity of the eyes of an observer.

This arrangement is not to be understood to be limiting. In general, the stereo base results from distal apertures of the lens unit and/or their distance from each other. This is also relevant for the position of the image sensors and/or their distance from each other, at least in certain embodiments.

In certain embodiments, in the case of mono-representation and/or 2D observation, only one of the two channels, i.e. only one of the two image sensors is used. This does not necessarily mean that only one of the two image sensors actually delivers a signal. However, at least in the case of image representation only the signal of one of the two channels is used.

In certain embodiments, the orientation of the instrument is detected by the position sensor in relation to a reference, for example in relation to a horizon. The reference can be a generally valid (global) reference or a reference defined on a case-by-case basis. Generally, a horizon is used as a reference that reflects the position and orientation of both eyes of an observer.

In certain embodiments, in the first representation mode the first image data and the second image data are combined in such a way that a stereo representation (3D reproduction) is possible. In the second representation mode, either the first image data or the second image data are used to enable mono representation (2D reproduction).

At least according to exemplary embodiments, the observation instrument is a hand-held or hand-guided instrument. However, this is not to be understood to be limiting. According to an alternative embodiment, the observation instrument is mounted on a tripod or something similar. The orientation of the instrument, especially its roll orientation, can be changed directly by the operator and/or by a motor-driven mechanism. The method according to the present disclosure may be arranged accordingly.

In regard of the observation method, the above and other objects are achieved by a method of stereo observation, the method comprising the following steps:

providing an observation instrument comprising an image acquisition unit for detecting first image data and second image data, which can be combined for stereo observation, detecting an orientation, especially a rotation orientation, of the instrument in relation to a position reference, and operating the imaging system depending on the orientation of the instrument in a first representation mode or a second representation mode, comprising:

in the first representation mode, outputting an image signal comprising a stereo signal based on the first image data and the second image data, in the second representation mode, outputting an image signal comprising a mono signal, and erecting the output images as needed, depending on the detected orientation, at least in the second representation mode.

The method may also be referred to as an imaging method for stereo observation, at least in certain embodiments. It is to be understood that the method may be arranged in accordance with the exemplary embodiments of the imaging system that are described in the context of this disclosure, and vice versa.

In an exemplary embodiment, the method includes the provision of a control device to control the imaging system.

In a further exemplary embodiment of the method, the method comprises the provision of a stereo imaging system with an observation instrument configured for stereo observation, with at least one position sensor for detecting an orientation, for instance a rotation orientation, of the instrument, and with a control device, which, depending on the orientation of the instrument, can be operated at least in a first representation mode or in a second representation mode, wherein the control device is configured to output an image signal, which, in the first representation mode, comprises a stereo signal based on the first image data and the second image data, and, in the second representation mode, comprises a mono signal based on the first image data or the second image data, and wherein the control device is configured to use the image signal to erect output images in the second representation mode depending on the orientation.

In certain embodiments, in the first representation mode, the output images, at least in exemplary embodiments, are not erected, i.e. they are output non-erected. Accordingly, the displayed images would rotate together with the rotation angle (roll angle) of the instrument in relation to the position reference.

According to an exemplary embodiment of the imaging system or method, the control device is configured to orient output images in the second representation mode so that the orientation of the displayed image in relation to a display horizon does not change or only within defined limits. The result of the orientation is then the representation of erected images.

In this way, in certain embodiments, an image erection can be realized. In the context of the present disclosure, the term image erection describes a function, in which the reproduced image retains its orientation (top—bottom—right—left), even when the instrument is rotated, at least in certain embodiments. By way of example, this relates to a so-called rolling movement, i.e. a rotation of the image acquisition unit and/or a lens assembly coupled thereto. The rotation defines an axis for the rolling movement. For example, in the case of an endoscope, the rotation can be about the longitudinal axis of an instrument shaft. However, flexible or partially deflectable observation instruments are also known where no rigid longitudinal axis is installed. Furthermore, observation instruments with a shaft and an observation head mounted thereon are also known, in which the rotation is not about the longitudinal axis of the shaft but about an axis through the observation head. This axis is for example perpendicular to the longitudinal axis of the shaft.

According to another exemplary embodiment of the imaging system or method, the control device is adapted in the first representation mode to output images in a non-erected state, so that changes in the orientation of the instrument are associated with changes in the orientation of the images to be output.

In certain embodiments, the term "non-erected" is to be understood in the context of the present disclosure in such a way that the images to be output are output without erection, i.e. not erected. Accordingly, an object in the image to be output would also be rotated by 5° during representation when the instrument were rotated by 5° around its longitudinal axis.

In certain embodiments, it has been observed that under certain circumstances in the first representation mode slight rotation angles are acceptable, in which the stereoscopic effect (3D effect with depth impression) is perceptible to the observer and at the same time, the orientation in the image is slightly reduced. It is therefore proposed to maintain the stereoscopic representation in the first representation mode within a limited rotation angle (also referred to as roll angle). This makes the imaging system more tolerant to slight rotation movements.

According to another exemplary embodiment of the imaging system or method, the control device is operable in a first rotation angle range of the instrument in the first representation mode, wherein the control device is operable in a second rotation angle range of the instrument in the second representation mode. For example, the first rotation angle range includes at least one neutral position of the instrument in relation to the position reference. A rotation angle range is at least one defined subsection of the available rotation angle.

In certain embodiments, the neutral position comprises, for example, a parallel orientation of a connecting line between the two image sensors and/or the apertures of the two channels in relation to the horizontal (or an artificial horizon). It is to be understood that the neutral position and/or initial position may also be defined on a case-by-case basis, using suitable control elements.

For example, the neutral position includes an upright state (perpendicular to the stereo base) in relation to the position reference (for example the horizon). Starting from the neutral position the rotation angle can be measured. A roll angle is usually an angle that describes a rotation around a longitudinal axis (of a shaft and/or the image acquisition unit).

In certain embodiments, the horizon that defines the neutral position may be adjusted during operation, at least according to an exemplary embodiment. In this way, for example, it is possible to react to global movements by carrying the observation instrument along. This relates, for example, to a repositioning of the patient while carrying along the observation instrument. The adjustment of the artificial horizon can be used to largely maintain the position and orientation of other instruments in the displayed image, when the patient and the observation instrument are rotated, but these other instruments are not.

In certain embodiments, possible rotation angle ranges can be defined in degrees (in relation to a 360° full circle) or in hours and minutes in relation to a 12 o'clock dial. Accordingly, a neutral position corresponds to an orientation of 0° and/or 0 o'clock. A position rotated with respect thereto by 180° corresponds to an orientation of 180° and/or 6 o'clock. Intermediate positions for the rotation angle result accordingly. In an exemplary embodiment, the first rotation angle range and the second rotation angle range complement each other to 360°.

For example, the first rotation angle range comprises a range between 11 o'clock and 1 o'clock and/or 330° and 30°. Accordingly, the second rotation angle range can cover a range between 1 o'clock and 11 o'clock and/or between 30° and 330°. The instrument would then be fully rotatable around its longitudinal axis. This is not to be understood to be limiting.

In certain embodiments, it is also conceivable, however, to make the instrument not completely rotatable around its longitudinal axis (and/or to configure the image erection only for such a partial area). By way of example, a partial area between 9 and 3 o'clock and/or 270° and 90° is considered. Accordingly, the first rotation angle range may also include a range between 11 and 1 o'clock and/or 330° and 30°. However, the second rotation angle range then includes (partial) sections between 9 and 11 o'clock and between 1 and 3 o'clock (corresponding to a first section between 270° and 330° and a second section between 30° and 90°).

According to another exemplary embodiment of the imaging system or the method, the first rotation angle range has two sections that are offset to each other by 180°. When the instrument is rotated 180° from the neutral position, the image acquisition unit and/or the two image sensors for the first and second image data are again aligned parallel to the position reference (horizon). The image sensors are reversed. Such a rolling movement by approximately 180° is generally called a flip. A stereo representation is also possible in the 180° staggered section. This may also include a (static) image erection. For an image erection, the image information (first and second image data) for the first observation channel and the second observation channel would have to be swapped (right with left swap, and vice versa), and the sections (right and left) would have to be rotated by 180° individually. Nevertheless, in addition to this "static" image erection, there is no continuous erection for small rotations departing from 180°.

In certain embodiments, accordingly, the first rotation angle range comprises a range with two sections. A first section is for example between 11 o'clock and 1 o'clock and/or 330° and 30°. A second section is given between 5 and 7 o'clock and/or 150° and 210°. Accordingly, the second rotation angle range comprises a first section and a second section. The first section comprises a range between 1 and 5 o'clock and/or between 30° and 150°. The second section has a range between 7 and 11 o'clock and/or between 210° and 330°. The second section comprises a range between 7 and 11 o'clock and between 210° and 330°. The range between 11 and 1 o'clock (and/or 330° and 30°) and between 5 and 7 o'clock (and/or 150° and 210°) then allows stereoscopic observation and image reproduction. It is understood that the above information for the first rotation angle range and the second rotation angle range is of an exemplary nature and is not to be understood to be limiting. The first rotation angle range can be aligned symmetrically to the vertical (0° position). In addition, however, non-symmetrical angle ranges are also conceivable in relation to the vertical.

According to another exemplary embodiment of the imaging system or method, the control device is configured to swap the first image signal and the second image signal and to rotate the first image signal and the second image signal by approximately 180°.

In certain embodiments, this may be done in the section of the first rotation angle range that is 180° opposite the neutral position. In this way, a static image erection with 3D function may be provided even during a flip.

In certain embodiments, accordingly, the first representation mode according to this exemplary embodiment comprises two operating modes. The first mode relates to an original orientation in accordance with the position reference (which defines the neutral position, for example). The second mode is the flip mode (180° rotation). Accordingly, the first section may also be referred to as the reference section and the second section the flip section.

According to another exemplary embodiment of the imaging system or method, the second rotation angle range comprises at least one position of the instrument that is rotated by 90° with respect to the position reference. This also applies to a 270° rotated position. At least in such a range (roll angle of 90° and/or 270°) the stereo functionality is not easily usable, if an upright image is desired. It is therefore reasonable to use only one observation channel in this range to output a 2D image. This image can then be electronically rotated, at least in exemplary embodiments, to erect the image, if required.

According to another exemplary embodiment of the imaging system or method, the first rotation angle range comprises, in terms of an angular scale where 0° (degrees) indicates an ideal orientation of the instrument in relation to the position reference, a first section covering a range with a first limit between 310° and 350° and a second limit between 10° and 50°, and wherein the first rotation angle range preferably comprises a second section that is offset by 180° with respect to the first section.

In certain embodiments, for example, the first rotation angle range is symmetrically arranged in relation to a vertical (at 0°). Accordingly, the first rotation angle range covers a range between +/−10° (plus/minus 10° and +/−50° in relation to the vertical, i.e. it covers 0°+/−10° for a small range and 0°+/−50° for a large range. For example, the first rotation angle range covers a range of 0°+/−45°. In another example, the first rotation angle range covers a range of 0°+/−30°. Accordingly, the second section can cover a range from 180°+/−10° up to 180°+/−50°, for example 180°+/−30° or 180°+/−45°.

In certain embodiments, in absolute terms, the first section of the first rotation angle range in an exemplary embodiment extends between 330° and 30°, wherein the second section of the first rotation angle range extends between 150° and 210°. The second rotation angle range, in which the instrument can be operated in the second representation mode, can be complementary to the first rotation angle range, for example with a first section between 30° and 150° and a second section between 210° and 330°.

In another exemplary embodiment, the first section of the first rotation angle range extends between 315° and 45°, wherein the second section of the first rotation angle range extends between 135° and 225°. Accordingly, the second rotation angle range in this exemplary embodiment comprises a first section between 45° and 135° and a second section between 225° and 315°.

In a third exemplary embodiment, the first section of the first rotation angle range extends between 345° and 15°, wherein the second section of the first rotation angle range extends between 165° and 195°. Accordingly, the second rotation angle range in this exemplary embodiment comprises a first section between 15° and 165° and a second section between 195° and 345°.

It is understood that other exemplary embodiments for the first rotation angle range, i.e. the first representation mode, and the second rotation angle range, i.e. the second representation mode, are also conceivable.

In certain embodiments, the first rotation angle range, i.e. the range with stereo representation but without comprehensive image erection, is selected in such a way that the operator can still orientate himself well in the image, which is often the case with a slightly tilted position. This may have the advantage of stereo representation, is in some embodiments. Depending on the specific use of the imaging system and/or depending on the objective and subjective preferences of different operators, the first rotation angle range and/or the second rotation angle range can be defined.

In certain embodiments, it is conceivable to fix the first rotation angle range. It is also conceivable to have a small number of variants for the first rotation angle range (approximately +/−30° or +/−45°, each with respect to the vertical—at 0° and, if necessary, at 180°), which the operator can choose between. It is also conceivable to give the operator the possibility of freely defining the first rotation angle range and thus also the second rotation angle range within wide limits.

In certain embodiments, in general, the sections can cover ranges of at least 355° to 5° (i.e. at least +/−5°) and at least 175° to 185°. This includes exemplary embodiments where the first angle range comprises values between +/−30° and +/−45°, each with respect to a 0° position and, if necessary, a 180° position. However, this is not to be understood as a limitation. Other angle ranges are conceivable. If one of the two rotation angle ranges is defined, the corresponding other rotation angle range can be derived. In this example, the two rotation angle ranges complement each other to 360°. At the full circle, each of the two rotation angle ranges may be provided twice, offset by 180°.

According to another exemplary embodiment, the first rotation angle range section comprises between 315° and 45° and between 135° and 225°. Thus, the second rotation angle range includes angle sections between 45° and 135° and between 215° and 315°. According to another exemplary embodiment, the first rotation angle range sections are between 330° and 30° and between 150° and 210°. Thus, the second rotation angle range sections are between 30° and 150° and between 210° and 330°. However, this is not to be understood to be limiting.

According to another exemplary embodiment of the imaging system or method, the control device is operable to enable an adapted transition when switching between the first representation mode and the second representation mode, wherein the transition preferably comprises an adaptation between the orientation of the mono signal in the second representation mode and the orientation of the stereo signal in the first representation mode at a switching angle between the first representation mode and the second representation mode.

In certain embodiments, the transition (also known as transition mode) makes the change between the stereo representation and the 2D representation more harmonious for the operator. Image signals output in the first representation mode (stereo) are regularly processed separately for the right and left eye. This can include, for example, fields of view that show the object under observation from two slightly different angles. When switching between the first representation mode and the second representation mode (and vice versa), there is therefore a change between a display with two different fields and a display with uniform images for the right and left eye. For example, during the transition, one of the two fields is deliberately faded out, whereupon the other field becomes decisive for both eyes (and vice versa in the other representation mode).

According to another exemplary embodiment of the imaging system or method, the control device is configured, in the second representation mode, to orient output images dependent on the rotation angle, so that preferably a low-skip or skip-free transition between the first representation mode and the second representation mode is produced.

In certain embodiments, in this way, a steady or almost steady transition without a "jumping" image is made possible. There are preferably no jumping changes in the rotation orientation of the image when the instrument is rotated and there is a change between the first and second representation mode. In other words, a low-skip or skip-free transition, in terms of the rotation angle, between the first representation mode and the second representation mode is possible, at least in exemplary embodiments. It is understood that smaller jumps may be quite acceptable and possible. However, these jumps should not have a negative effect on the visual orientation of the observer in the displayed image.

In certain embodiments, this design may take account of the fact that, at least in exemplary embodiments, the first representation mode includes tolerant angular ranges (approximately 330° to 30° or even larger), in which the image is stereoscopically captured and reproduced in the object plane, wherein in this (small) range a strict erection of the image is dispensed with. Stereo representation is regularly only useful if the displayed image rotates together with the rotation of the instrument.

If, however, the user then leaves the first angular range, in which the first representation mode is possible, then an abrupt transition to the second representation mode would possibly result in an immediate erection of the image in relation to the position reference, at least in certain embodiments. This may have the consequence that the image would "jump forward" and/or "jump back" from the observer's point of view. Therefore, at least in exemplary embodiments it is intended to provide a transfer mode to make this transition less abrupt.

According to another exemplary embodiment of the imaging system or the method, the control device interpolates, in the second representation mode, the images to be output between the non-erected state and the erected state.

In this way, the transition can be made smooth and ideally jerk-free or with low jerks by means of suitable interpolation steps, at least in certain embodiments. This may improve perception and avoids excessive visual stress for the user during observation.

In certain embodiments, depending on the rotation angle of the instrument, the orientation of the image to be output changes, but the image is still erected. The interpolation of the images (and/or the interpolation of the orientation of the images) helps to avoid or at least reduce jumps at the transition between the first representation mode and the second representation mode. For example, interpolation is performed between an actual rotation at the transition between the first representation mode and the second representation mode and a nominal orientation, which corresponds to the (ideal or nearly ideal) erected image.

In certain embodiments, this means that immediately at the transition between the first representation mode and the second representation mode there is no "jump" of the image and/or abrupt rotation of the image. Instead, the image is continuously moved and/or rotated. Thus, the observer notices the change between the first representation mode and the second representation mode (which also includes a change between 3D and 2D). Furthermore, the first representation mode can be made sufficiently tolerant with the stereoscopic representation, so that the stereo effect is not only possible with absolutely exact orientation of the image acquisition unit in relation to the position reference.

According to another exemplary embodiment of the imaging system or the method, the control device is configured to erect images to be output in the second representation mode between a switching angle, which is assigned to the transition between the first representation mode and the second representation mode, and in which for example the image assumes an orientation corresponding to the switching angle, and a limit angle or limit angle range of the instrument in the second representation mode.

In certain embodiments, by way of example, the limit angle describes a range, in which the reproduced image is fully erected, i.e. in which the orientation of the reproduced image corresponds to the nominal orientation defined by the position reference and/or a selected artificial horizon. By way of example, the limit angle is associated with an instrument rotation orientation of 90° and 270°. Therefore, there can be two limit angles. It is also conceivable to offer the complete erection of the image in a limit angle range, i.e. not only at a certain angular position. Such a limit angle range could cover a range of 90°+/−15°. A complementary, second limit angle range can cover a range of 270°+/−15°. This means that when the instrument is rotated within this range, the image displayed does not change its erection, or only slightly.

According to another exemplary embodiment of the imaging system or method, the switching angle, in terms of an angular scale, in which 0° indicates an ideal orientation of the instrument in relation to the position reference, is between 25° and 50°, for instance between 30° and 45°. If the first angular range is symmetrical, there is accordingly a further switching angle symmetrical to the vertical, for example in the range between 310° and 335°, for instance at 315° to 330°. The switching angles correspond in an exemplary embodiment to the limits of the first rotation angle range in the first representation mode.

According to another exemplary embodiment of the imaging system or method, the control device is configured to rotate images to be output in the second representation mode between the limit angle or limit angle range and a further switching angle in such a way that the orientation of the displayed image is adapted to the further switching angle when the instrument is rotated towards the further switching angle.

In certain embodiments, the further switching angle describes the transition between the second representation mode and the first representation mode in an upside down orientation of the instrument, wherein in view of the at least approximately 180° rotated position of the instrument for stereoscopic representation, the first image signal and the second image signal are exchanged and each rotated by 180°, at least in an exemplary embodiment. The image is basically upright, but certain rotation angles are tolerated for a robust stereo representation.

In an exemplary embodiment, the reproduced image is therefore not shown in a state rotated beyond the (first) switching angle. In a first example, this means that in the first representation mode as well as in the second representation mode the displayed image is only shown in a state rotated within +/−45°. In another exemplary embodiment, in the first representation mode as well as in the second representation mode, the displayed image is only shown in a state rotated within +/−30°.

According to another exemplary embodiment of the imaging system or method, the further switching angle, in terms of an angular scale, in which 0° indicates an ideal orientation of the instrument in relation to the position reference, is between 130° and 155°, for instance between 135° and 150°, with a limit angle of approximately 90°. With a symmetrical orientation of the first angular range, there is accordingly a further switching angle symmetrical to the vertical, for example in the range between 205° and 230°, for instance between 210° and 225°.

According to another exemplary embodiment of the instrument, the control device allows a change of the position reference, especially a change from an ideal position reference given by the orientation of the image acquisition unit. Usually, the position reference results from the arrangement of the two apertures of the image acquisition unit. For example, the instrument is in an ideal orientation, in which an observer can stereoscopically perceive an upright image if the two apertures are offset from each other in a horizontal plane (horizontal orientation of the stereo base).

Accordingly, in certain embodiments, this orientation would also be the reference for the image erection in the second representation mode. However, there are also known applications where an adjustment of the position reference is desired. This may be the case, for example, if the observation object (for example, the patient) is repositioned, but at the same time, the assignment between the observation object and the image output (erected) by the observation instrument should be maintained. In this case, an artificial horizon can be defined, which results from a selected offset (offset angle) with respect to the original horizon (for example in the ideal orientation).

In certain embodiments, in such an operating mode with adjusted artificial horizon, the new adjusted artificial horizon can now represent the new position reference for the orientation of the instrument. In the second representation mode, the displayed images can be erected under consideration of the new position reference. It is understood that in the first representation mode with changed artificial horizon the physical orientation of the image acquisition unit is not changed. When switching from the second representation mode to the first representation mode, there is a transition between the erected 2D image and the non-erected stereoscopic image. The image would therefore jump "forward" or "backward", wherein the transition can be made smooth, as described further above. Whether the image jumps "forward" or "backward" depends on the direction of rotation. A similar situation can arise if the first representation mode includes a second section (flip position) offset by 180° to the first section (neutral position).

For detecting the rotational position/orientation of the image acquisition unit, at least one position sensor is provided, in certain embodiments. The position sensor detects a rolling position (rotation around the longitudinal axis) of the observation instrument and/or the image acquisition unit. In the case of a stereo endoscope, the position sensor detects a rolling position of the instrument shaft, by way of example.

Various designs of the position sensor are conceivable. This may include one or more acceleration sensors. Acceleration sensors can detect relative positions. For detecting an absolute position/orientation, gyroscopes or similar sensors are suitable. It is understood that the position sensor can include at least one discrete sensor. The position sensor is arranged in the instrument in exemplary embodiments. For example, the position sensor is located in the shaft of the instrument, in the handle or in the observation head.

In certain embodiments, the position sensor can be located at the proximal or distal end of the instrument. If several sensors are installed, they may be spatially distributed. A spatial distribution allows the detection of the position and/or orientation under consideration the relative orientation between the position sensors.

In certain embodiments, however, it is also conceivable to implement the position sensor at least partially by means of software. The position sensor does not necessarily have to be a discrete sensor. The position sensor may also be a tracker located on or in the instrument, which is detected by an external navigation system optically, via magnetic field changes or direct electro-magnetic signal transmissions, and which enables the calculation of the position of the instrument. A position of the captured and reproduced image may also be detected by image processing operations, especially when tracking a movement. This may include pattern recognition, for example, so that a position is determined in the image and this position is constantly maintained during the movement of the instrument and/or the image acquisition unit, at least in the second representation mode.

According to another exemplary embodiment of the imaging system or method, the observation instrument is arranged as an instrument with an inclined direction of view. For the purposes of the present disclosure, an inclined direction of view is understood to be, for example, an inclination of an optical axis of the lens in relation to a longitudinal axis (axis of rotation) of the shaft.

In certain embodiments, instruments with, for example, 10°, 15°, 20° 30° or 45° inclined direction of view are known. Such angles of inclination are also conceivable in the context of the present disclosure. However, this is not to be understood in a restrictive way. At least in exemplary embodiments, the term inclined direction of view does not include an absolutely lateral direction of view (tilted 90° with respect to the longitudinal axis). Such instruments are called lateral view instruments.

In certain embodiments, instruments with variable direction of view are also known, where an angle of inclination is adjustable in relation to the longitudinal axis. An instrument with an inclined direction of view may also referred to as an oblique viewing instrument. The angle of inclination of the direction of view covers exemplary ranges between 10° and 60° in relation to the longitudinal axis.

In certain embodiments, instruments with inclined direction of view present special challenges during rolling movement around the shaft axis when stereoscopic observation is required. Instruments with inclined direction of view are often deliberately rotated around the shaft axis to vary the current field of view and/or to change the display of objects in the field of view. In this way, different ranges and/or objects of observation can be observed depending on the respective roll angle. This means, however, at least in exemplary embodiments, that certain sections of the rotation ranges can be recorded stereoscopically, whereas other sections can only be acquired and reproduced monoscopic, at least when an image erection is desired.

In certain embodiments, if, in the case of stereoscopic observation, the individual images are each erected separately, then the orientation of the stereo base would also have to be adjusted depending on the rotation angle, when the instrument is rotated (rolling movement), so that stereoscopic observation with the right and left eye is possible. Accordingly, an additional, combined, internal pivoting movement of the image sensors and/or the lenses of the image acquisition unit would be necessary to adjust the stereo base to the desired image orientation during representation and the given rotation orientation of the image acquisition unit. However, this is hardly implementable by mechanical means. In addition, the inclined direction of view makes the composition of an erected stereo image for any rotation orientations of the image acquisition unit more difficult.

According to another exemplary embodiment of the imaging system or method, the observation instrument carries the image acquisition unit, wherein the image acquisition unit comprises a stereo image sensor or two individual sensors that are offset from each other.

In certain embodiments, the sensors of the image acquisition unit are exemplarily arranged at or near the distal end of the instrument and/or its shaft. According to an alternative embodiment, the sensors of the image acquisition unit are arranged at or near the proximal end of the instrument and/or its shaft.

According to another exemplary embodiment, the imaging system also has a display unit with at least one display, for instance a 3D screen and/or 3D glasses. 3D glasses can be used in combination with a 3D display screen, by way of example. However, 3D glasses are also known to have their own displays. Such display units are known as HMDs (Head Mounted Display). The method in accordance with the present disclosure may use such devices.

In certain embodiments, the display is suitable for representation in stereo mode (3D playback) using the image data of both observation channels and also for representation in mono mode (2D playback) using the image data of only one observation channel.

In certain embodiments, overall, the instrument may be operated in various global modes, at least in certain embodiments. In an exemplary design, there are four global operating modes.

In certain embodiments, in a first global mode, the instrument can be operated, on demand, at least in the first representation mode (stereo representation) and in the second representation mode (mono representation) in order to enable stereo representation, if possible, and mono representation including image erection, if required, in areas without stereo representation. It is understood that transitional modes in accordance with the present disclosure are also conceivable, at least in exemplary embodiments.

In certain embodiments, in a second global mode, the instrument can be operated in the second representation mode (mono representation), wherein image erection is performed. In an exemplary embodiment, this means that stereo representation is not used in this mode.

In certain embodiments, in a third global mode, the instrument can also be operated in a mono representation mode (representation of only one field). However, the third global mode does not include straightening. In an exemplary embodiment, this means that stereo representation is not used in this mode.

In certain embodiments, in a fourth global mode, the instrument can be operated in the first representation mode (stereo representation). In an exemplary embodiment, this includes no image erection. In an exemplary embodiment, this means that mono representation is not used in this mode.

It is understood that certain embodiments involve the use of two, three or four of the global modes.

In regard of the computer program, there is presented a computer program comprising program code that is arranged to cause an imaging system to perform the steps of the method according to one of the embodiments described herein, when the computer program is executed on the control device of the imaging system.

In regard of the storage medium, there is presented a non-transitory computer-readable storage medium including computer program instructions, which when executed by a control device of an imaging system, cause the imaging system to perform the steps of the observation method according to one of the embodiments described herein.

It is to be understood that the above-mentioned features of the invention and those to be explained in the following can be applied not only in the respectively specified combination, but also in other combinations or singly, without departing from the scope of the present invention.

BRIEF DESCRIPTION OF THE DRAWINGS

Further features and advantages of the invention are disclosed by the following description of a plurality of exemplary embodiments, with reference to the drawings, wherein:

FIG. 3: is a perspective front view of an observation instrument in the form of an exoscope;

FIG. 4: is a broken lateral partial view of the instrument as shown in FIG. 3;

FIG. 9 to FIG. 14:

Figure 15:
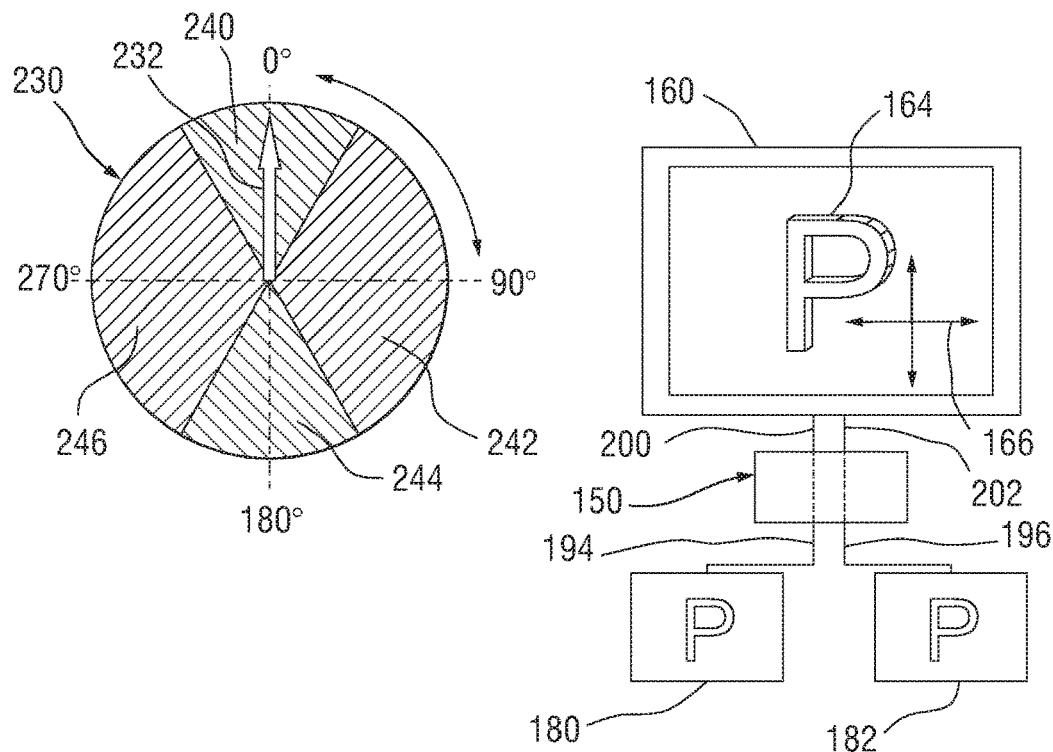
Figure 16:
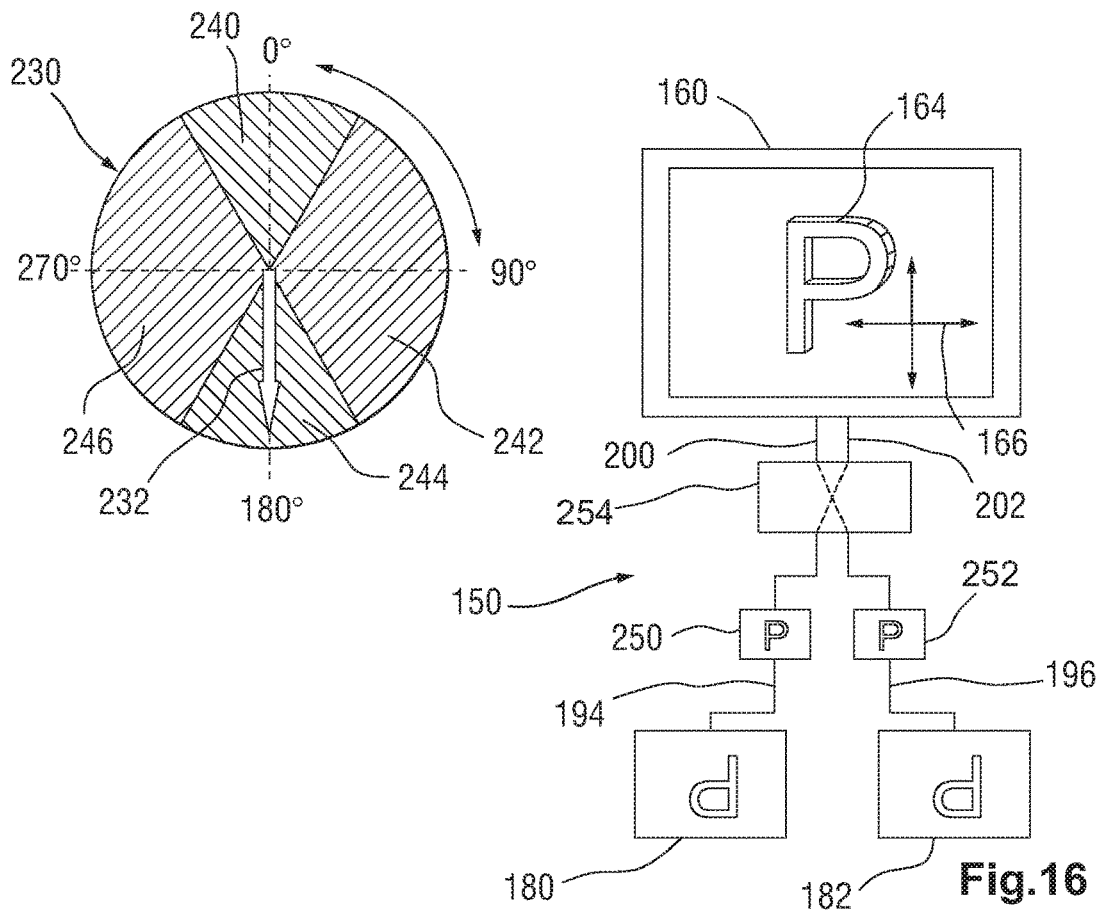
Figure 17:
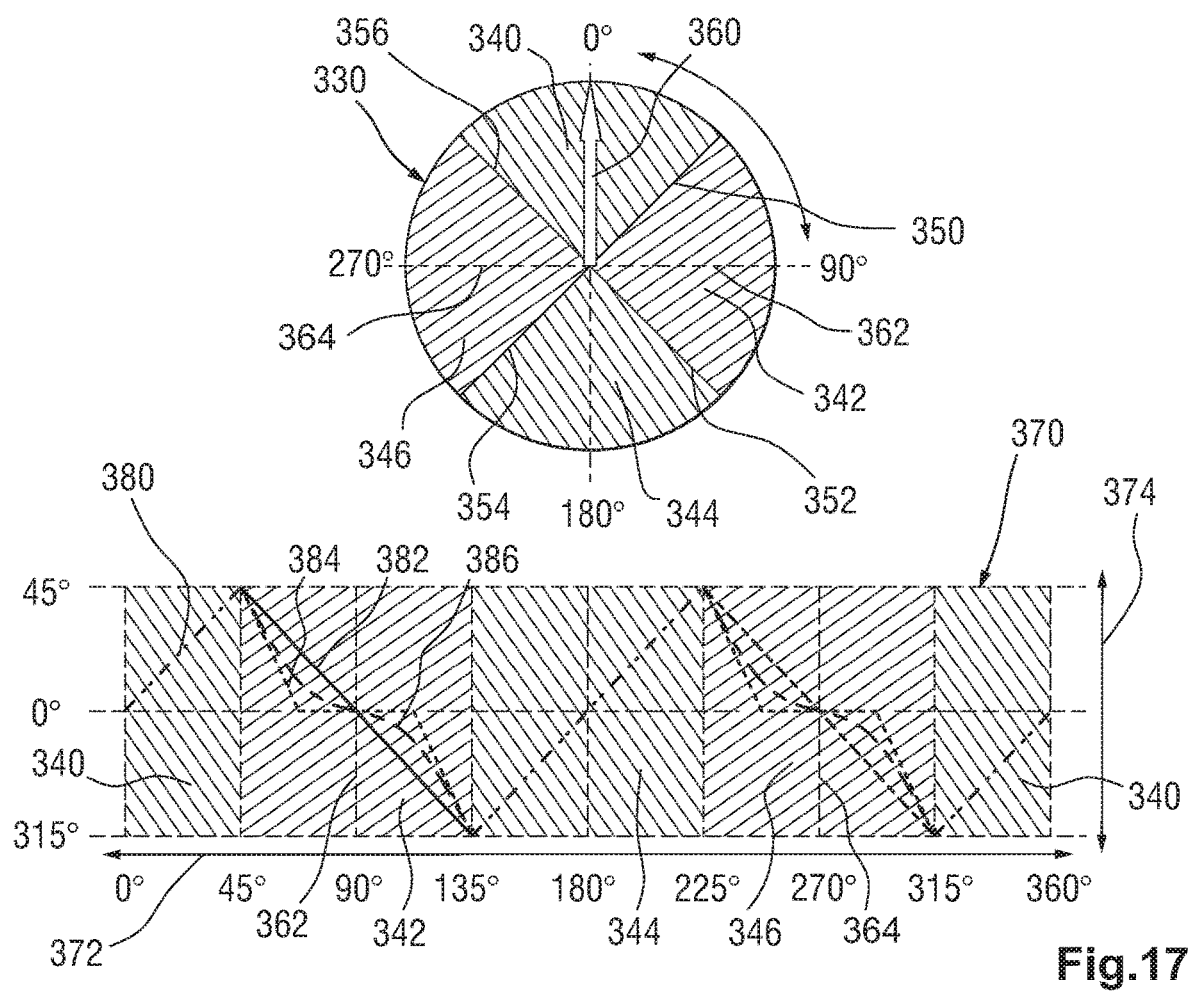
Figure 18:
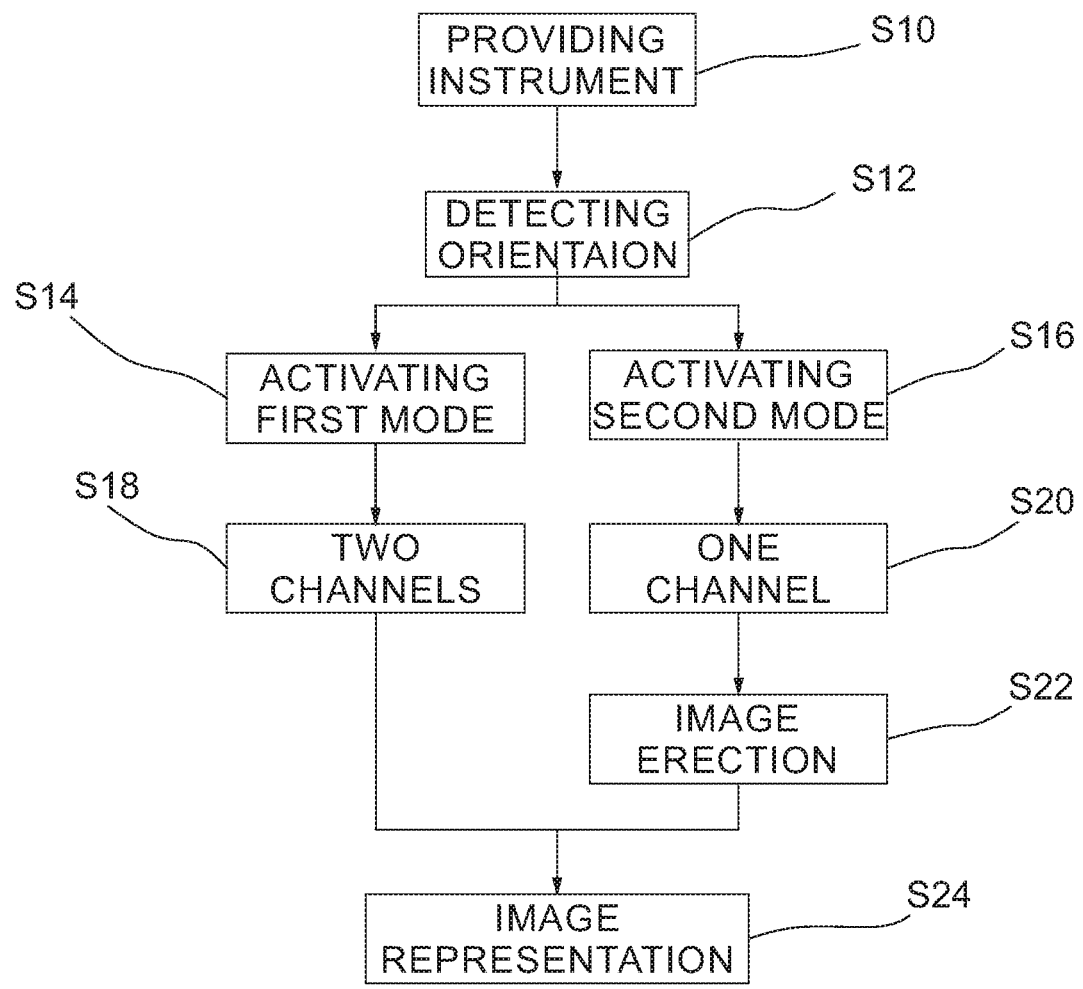
Figure 19:
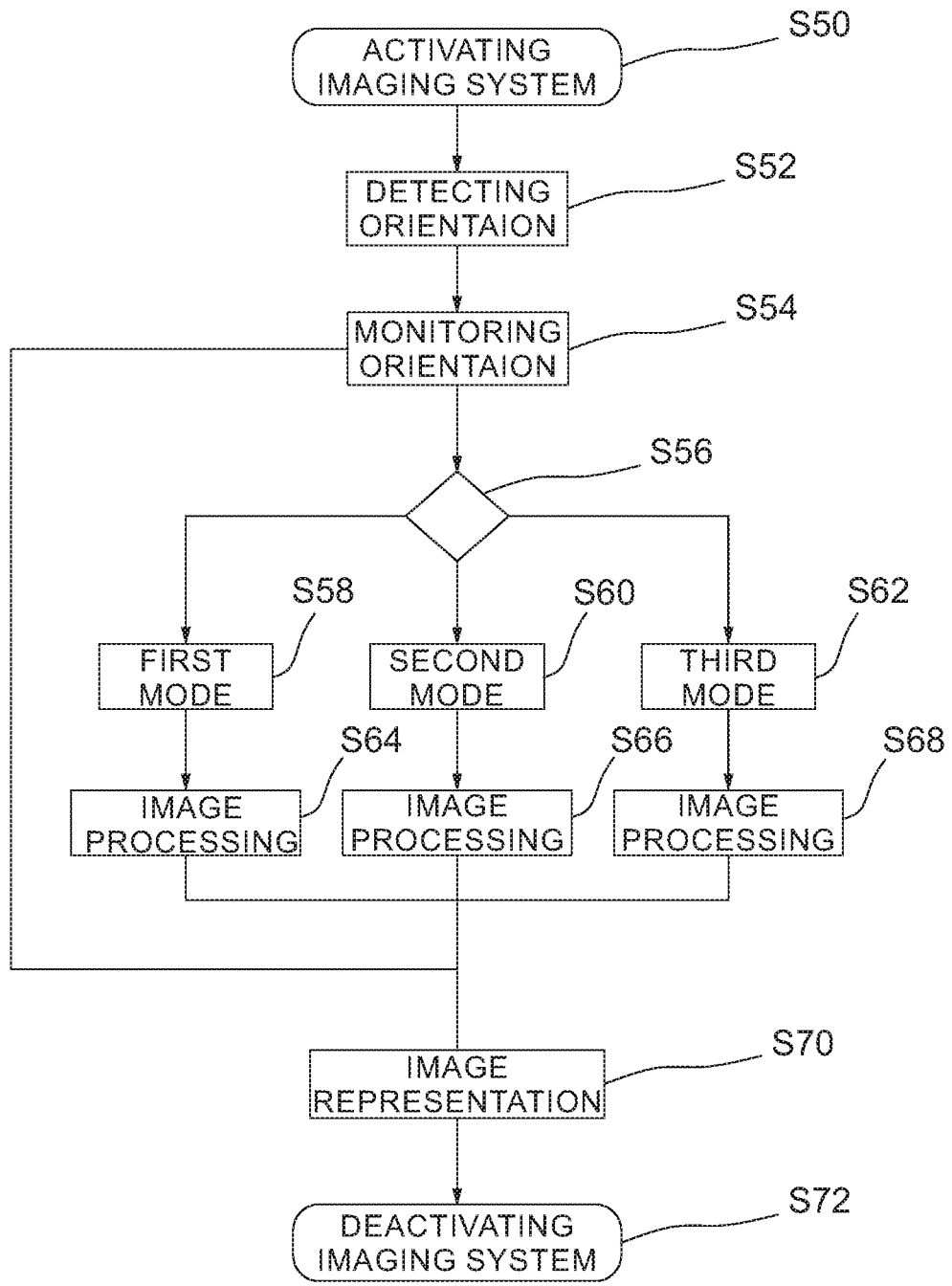

are several simplified schematic representations illustrating the relationship between a display mode and a current rotation orientation of an observation instrument;

FIG. 15: is a simplified schematic view illustrating image composition during stereo representation;

FIG. 16: is a further illustration of the arrangement according to FIG. 15, illustrating the composition of the image when rotated by 180°;

FIG. 17: is another simplified schematic view illustrating a switching between a first representation mode and a second representation mode;

FIG. 18: is a schematically simplified block diagram illustrating an embodiment of a method for stereo observation with an observation instrument; and FIG. 19: is another schematically simplified block diagram illustrating a further embodiment of a method for stereo observation with an observation instrument.

EMBODIMENTS

Figure 1:
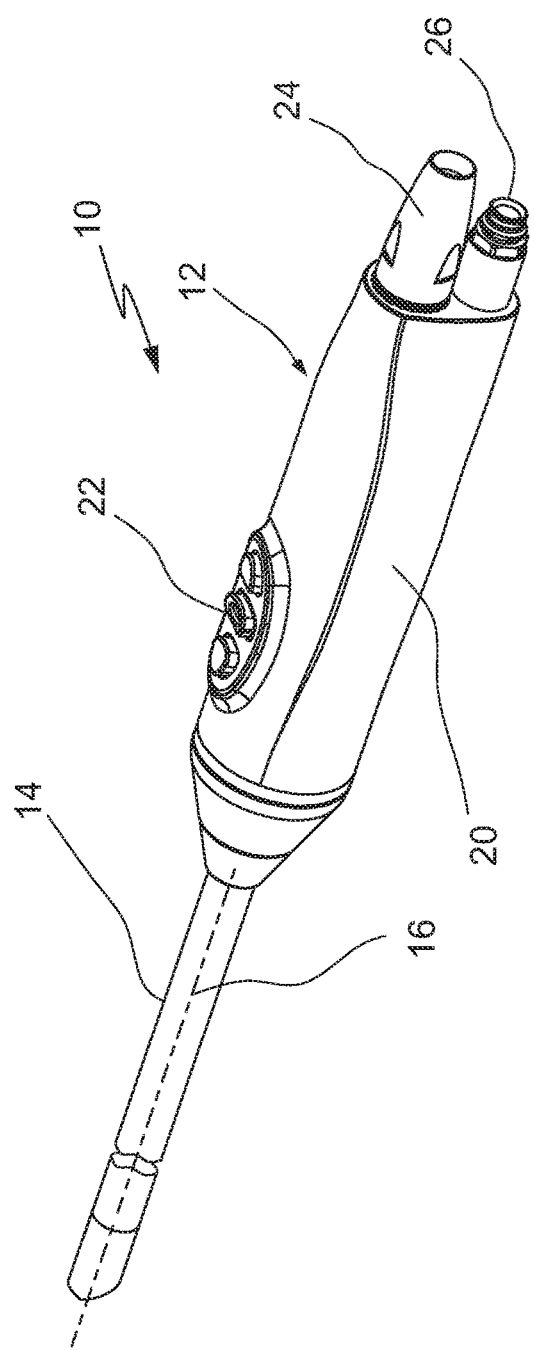
FIG. 1: is a broken perspective rear view of an observation instrument in the form of an endoscope.
Figure 2:
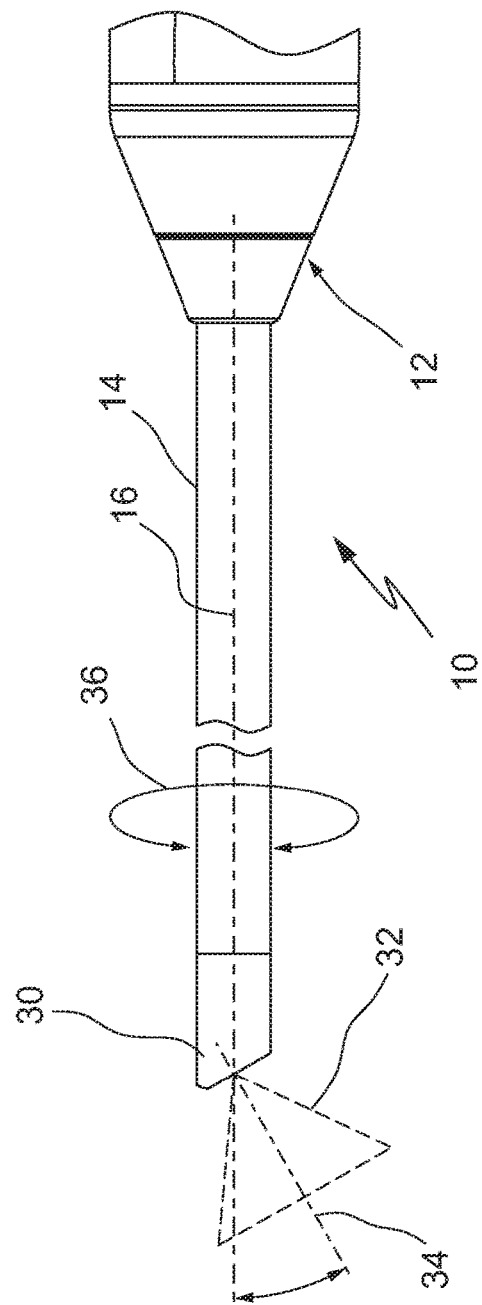
FIG. 2: is a broken lateral partial view of the instrument as shown in FIG. 1.

FIG. 1 shows a perspective view of an exemplary embodiment of an observation instrument 10 in the form of an endoscope 12. FIG. 2 shows a corresponding partial view from the side. The observation instrument 10 is exemplarily designed as a stereo endoscope 12. The endoscope 12 is configured to observe the inside of the body.

Medical and non-medical (technical) applications for endoscopes 12 and similar observation instruments 10 are generally known. The endoscope 12 comprises a shaft 14, which defines a longitudinal axis 16. By way of example, the shaft 14 comprises a distal end and a proximal end. In the context of the present disclosure, a distal end is an end facing away from the observer (operator of the instrument) and facing the object of observation. Furthermore, in the context of the present disclosure, a proximal end is an end facing away from the object of observation and facing the observer (operator of the instrument).

At the proximal end of the shaft 14, the endoscope 12 comprises a housing 20. The operator can grip and guide the endoscope 12 in the area of the housing 20. When used as a medical instrument 10 for observing the inside of the body, the shaft 14 of instrument 10 can be at least partially inserted into a natural or artificial body orifice.

The housing 20 comprises, for example, operating elements 22 and connections 24, 26. Connections 24, 26 concern, for example, an electrical supply line, a signal line, a lighting connection, as well as connections for liquids or gases that are required during medical procedures.

FIG. 2 illustrates that the instrument 10 is exemplarily designed as an inclined view endoscope 12. At the distal end of the shaft 14, an image acquisition unit 30 with a cone of vision/field of view 32 is indicated. The field of view 32 and/or its center (axis 34) is inclined with respect to the longitudinal axis 16. Angles of inclination can be at 30°, 45°, 60° and the like. Larger or smaller inclination angles are also conceivable. Inclined view endoscopes 12 with adjustable direction of view (adjustable angle of inclination) are also known. The axis 34 is exemplarily arranged as a normal to the sensor surface of the image acquisition unit 30.

Furthermore, in FIG. 2 a double arrow marked 36 illustrates a rotational movement of the instrument 10 around the longitudinal axis 16 of the shaft 14. Such a movement may be referred to as a rolling movement. Accordingly, the longitudinal axis 16 in this exemplary embodiment is a rolling axis. The movement according to the arrow 36 also rotates the image acquisition unit 30, which is inclined with respect to the longitudinal axis 16. Accordingly, such a rolling movement allows a significantly larger range of an object field to be observed, even if instrument 10 is not otherwise moved.

FIGS. 3 and 4 illustrate another observation instrument 50, which is designed as an exoscope 52. By way of example, the instrument 50 is a stereo exoscope 52, which comprises a shaft 54 with a longitudinal axis 56. At the proximal end of the shaft 54, the exoscope 52 comprises a housing 60 with control elements 62. Furthermore, connections 64, 66 are formed on the housing 60, especially at its proximal end. The exoscope 52 may also be held by the operator in the area of the housing 60 and thus guided and positioned. It is also conceivable that the exoscope 52 could be mounted on a tripod or similar. This could be a passive tripod (without the provision of motorized adjustment) or an active manipulator (comparable to a robot). However, also the use as a hand-held/handguided instrument 50 is conceivable.

At the distal end of the shaft 54, the instrument 50 comprises an observation head 68 with an image acquisition unit 70. The image acquisition unit 70 in the exemplary embodiment comprises a field of view and/or a viewing cone 72, the axis of which is designated by 74. In the exemplary embodiment as shown in FIGS. 3 and 4, the axis 74 is aligned approximately perpendicular to the longitudinal axis 56 along the shaft 54. Axis 74 is a normal to a sensor surface of the image acquisition unit 70, but this is not to be understood to be limiting. Axis 74 may also be an optical axis of the optical arrangement of the image acquisition unit 70, regardless of how the image sensor(s) is/are aligned.

Further, FIG. 4, a working distance is indicated by 78. It is understood that the working distance 78 in relation to the other dimensions of the instrument 50 does not necessarily have to be illustrated true to scale. In general, the exoscope 52 according to FIGS. 3 and 4, in contrast to the Endoscope 12 according to FIGS. 1 and 2, is configured to observe an object (patient, technical object) from the outside (outside the body). In this respect, exoscopes are similar to other observation instruments such as microscopes.

In FIG. 4, 76 also indicates a rotary motion/rolling motion of the image acquisition unit 70. It is conceivable to arrange the exoscope 52 in such a way that the image acquisition unit 70 can be rotated around the axis 74. In the case of an inclined view instrument, a different axis of rotation may be given. When designed according to FIGS. 3 and 4, the image acquisition unit 70 can be rotated in the observation head 68. Accordingly, the exoscope 52 is not rotated in its entirety. For rotation 76, a manual operation on the one hand and a motor operation on the other hand may be provided.

The working distance 78 of exoscopes is regularly significantly greater than that of endoscopes. For example, the working distance 78 can cover ranges from 100 mm (millimeters) up to 500 mm. However, this is not to be understood to be limiting. Usually exoscopes also have a sufficiently large depth of field, which is significantly greater than the depth of field of endoscopes. By way of example, the depth of field may include ranges of at least 5 mm, for instance at least 10 mm, and for instance at least 20 mm. However, this too should not be understood to be limiting.

By way of example, an exoscope 52 with a focus adjustment is provided. An endoscope 12 with a fixed depth of field of 20 mm is provided, by way of example. In other words, both exoscopes and endoscopes may be fitted with devices for adjusting the depth of focus. However, optical arrangements with a fixed depth of field are also conceivable.

For observation with the endoscope 12 as well as for observation with the exoscope 52, it is advantageous if stereoscopic imaging is possible, at least in some applications. A stereoscopic view allows an impression of depth (spatial impression) and facilitates navigation with other instruments in the observed range.

Accordingly, both endoscopes 12 and exoscopes 52 with 3D function (in the sense of stereoscopic observation) are known. Usually such instruments then comprise two image sensors offset to each other or a stereo sensor with corresponding offset sensor areas. Stereo observation is made possible by two observation channels with two spaced apertures, which are adapted to stereoscopic vision with the right eye and the left eye.

By way of example, for stereo representation so-called 3D monitors are known, which make a stereoscopic effect available by using specific means (3D glasses). Furthermore, so-called HMDs (Head Mounted Display) are known, i.e. video glasses with stereo effect that are worn by the observer himself.

Stereoscopic observation and representation, however, reaches its limits when the instrument is rolled and the stereo base (imaginary line by which the two sensors/sensor surfaces are offset from each other) changes relative to a reference horizon. This is especially the case when an image erection is desired. The reference horizon is usually defined by the arrangement of a display unit and finally by the arrangement of the human eyes (eye distance, disparity).

Thus, if the stereo base of the image acquisition unit no longer corresponds at least approximately to the reference horizon, the stereoscopic representation—while maintaining the image erection—can no longer be guaranteed with sufficiently high quality. This applies at least if an attempt is made to "artificially" maintain the orientation of the output image. Stereo observation without image erection is possible, but the orientation in the non-erected image becomes more difficult with increasing rotation angle. Therefore, it is not easily possible to implement measures for (digital) image erection in stereo observation instruments. The 3D image is regularly formed based on two observation channels. An image erection (digital/electronic or via a corresponding actuator for rotating the respective sensor) could now rotate the respective single image in the first channel and in the second channel in order to erect it. However, with large angular ranges, there would then no longer be sufficient correspondence between the reference horizon and the position of the stereo base. The present disclosure is concerned with this problem area.

Figure 5:
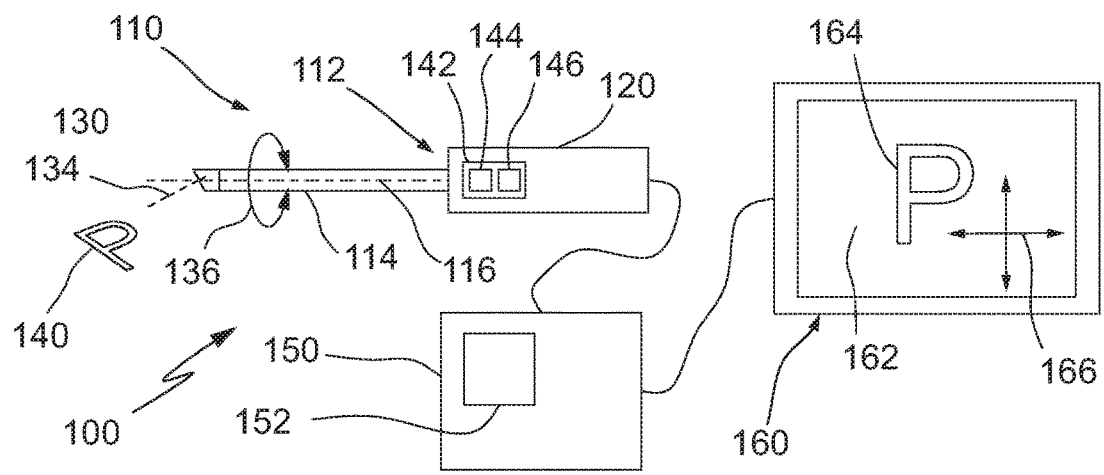
FIG. 5: is a simplified, schematic view of an imaging system with an observation instrument in the form of an endoscope.
Figure 6:
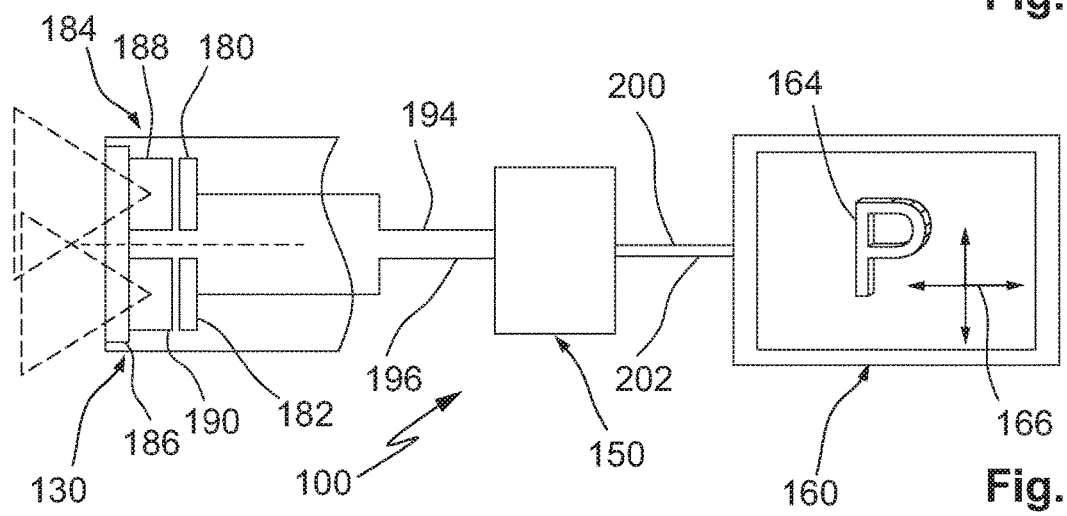
FIG. 6: is a simplified, schematic view of an imaging system with stereo functionality.

With reference to FIG. 5 and FIG. 6, by means of two schematically simplified block diagrams an exemplary embodiment of an imaging system 100 with an observation instrument 110 in the form of a stereo endoscope 112 is illustrated. The endoscope 112 comprises a shaft 114, which defines a longitudinal axis 116. At the distal end of the shaft 114, there is an image acquisition unit 130. In the exemplary embodiment according to FIG. 5, the image acquisition unit 130 is oriented inclined in relation to the shaft 114 in such a way that the axis 134 is inclined with respect to the longitudinal axis 116. The endoscope 112 also comprises a housing 120 at the proximal end of the shaft 114. The image acquisition unit 130 is targeted towards an observation object 140. The curved double arrow 136 in FIG. 5 illustrates a rolling movement of the instrument 112 about the longitudinal axis 116.

In the exemplary embodiment, the housing 120 also contains a sensor unit 142, which comprises a first sensor 144, by way of example. By way of example, the first sensor 144 is one or more acceleration sensors. In this way, changes in position/position of the instrument 110 can be detected. In addition, sensor unit 142 is equipped with a second sensor 146, for example a gyroscope. The sensors 144, 146 can be referred to as position sensors. Accordingly, the sensor unit 142 can comprise absolute measuring position sensors 146 and relative measuring position sensors 144. It is to be understood that the sensor unit 142 may also be provided at a different position on the instrument 112, for example close to the image acquisition unit 130. Other configurations of the sensor unit 142 with at least one position sensor 144, 146 are conceivable without further ado.

It is also conceivable to implement the sensor unit 142 or at least one of the position sensors 144, 146 outside the observation instrument 110. By way of example, a monitoring of the position/orientation of the instrument 110 may also be realized via external sensors (optical or electromagnetic tracking of markers, or the like). In principle, a digital implementation of at least one position sensor is also conceivable. This could include, for example, image-processing processes (pattern recognition, motion tracking, etc.). Combined arrangements for detecting the orientation, for instance the current roll position of the instrument and/or the image acquisition unit, are conceivable without further ado.

The instrument 110 is coupled via a signal line (wired or wireless) to a control device 150 with at least one control unit 152. The control device 150 may also be at least partially integrated into the instrument 110. However, the control device 150 may also be arranged as a separate control device. The control device 150 can generally be designed as a central or decentralized/distributed control device. The control device 150 is configured to receive data from instrument 110. This data is based on image information/image signals acquired with the image acquisition unit 130. The control device 150 is configured for data processing, for instance for processing and preparing image data.

An exemplary embodiment of a control device 150 is marketed by the applicant under the name "IMAGE1 S" as a so-called camera platform. Usually, a stereo observation system comprises, in addition to the instrument (endoscope or exoscope), such a camera platform and at least one display unit (such as a 3D monitor).

In the design according to FIG. 5, the control device 150 is in turn (wireless or wired) coupled via a signal line with a display unit 160 for stereo playback. The display unit 160 is exemplarily designed as monitor, especially as 3D monitor. It is understood that under certain circumstances further equipment, such as suitable glasses, may be required to view a 3D image (stereo image). The display unit 160 allows a representation of the observed object 140, cf. the reference sign 164 designating the displayed image. Further, in FIG. 5 a position reference is indicated by 166. The position reference 166 comprises at least one horizon or coordinate system, based on which the reproduced image 162 is oriented. With suitable orientation between the image acquisition unit 130, the observed object 140 and the displayed image 164 on the display 162 a stereoscopic representation is possible.

It is understood that the arrangement shown in FIG. 5 may also be supplemented by a light source or other units suitable for use with instrument 110.

In addition to FIG. 5, FIG. 6 shows further design features of the exemplary embodiment of imaging system 100. The image acquisition unit 130 is formed at the distal end of the shaft 114. The image acquisition unit 130 includes a first image sensor 180 and a second image sensor 182, which are also located at the distal end of the shaft 114 in the exemplary embodiment shown. However, this is not to be understood to be limiting. Embodiments with proximally arranged image sensors are also conceivable.

The image sensors 180, 182 are preceded by a lens assembly 184. The lens assembly 184 comprises, for example, a cover glass 186 and optical units 188, 190 with apertures, which are associated with the image sensors 180, 182. The optical units 188, 190 define the respective field of view of the image sensors 180, 182. Each of the two image sensors 180, 182 is associated with an observation channel 194, 196. One of the two observation channels 194, 196 can be referred to as right channel and the other as left channel. Accordingly, one of the two image sensors 180, 182 can be referred to as the right sensor and the other the left sensor.

In the exemplary embodiment shown in FIG. 6, the term observation channel does not necessarily refer to an optical observation channel. Instead, the channels 194, 196 are regularly designed as channels for transmitting image data to the control device 150, which are acquired by the right and left image sensors 180, 182. The control device 150 is used to process and prepare the image data. Further, two output channels 200, 202 are provided at the output of the control device 150, which in turn can be referred to as right and left output channels 200, 202. If image information (such as fields for the right and left eye) is provided via both output channels 200, 202, a suitable display unit 160 can be controlled for stereoscopic representation (3D display). FIG. 6 illustrates such a 3D representation of the observation object 164, which is also aligned in relation to the position reference 166.

Figure 7:
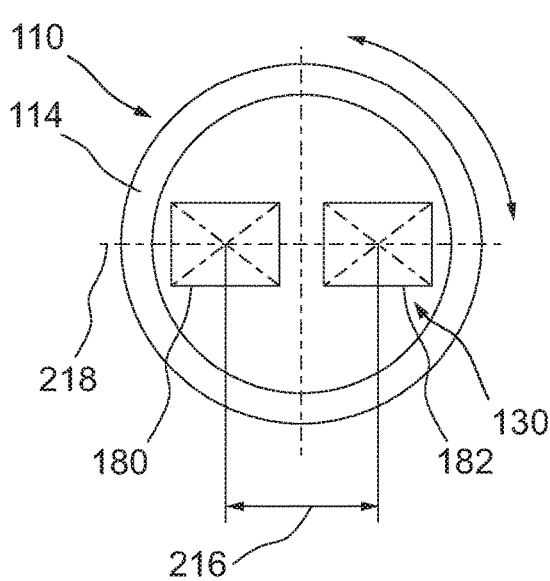
FIG. 7: is a frontal view of an image acquisition unit for stereo observation.
Figure 8:
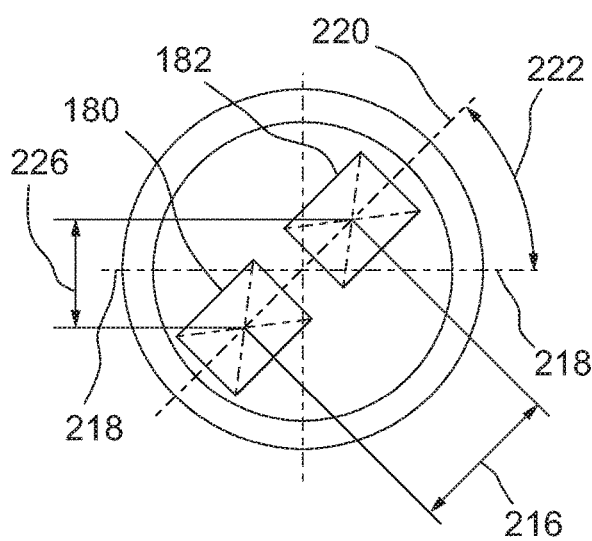
FIG. 8: is another view of the image acquisition unit according to FIG. 7 in a rotated representation, compared to FIG. 7.

FIG. 7 and FIG. 8 illustrate a frontal view of an exemplary embodiment of an image acquisition unit 130 with two image sensors 180, 182. In the exemplary embodiment shown, the image acquisition unit 130 is mounted in the shaft 114 of an instrument 110. However, this is not to be understood to be limiting. The two image sensors 180, 182 are separated from each other by a distance 216, which is adapted to the stereo base (e.g. distance between the apertures of the optical units 188, 190). The relative position of the two image sensors 180, 182 further defines a sensor horizon 218. If the sensor horizon 218 of the two image sensors 180, 182 coincides with the position reference 166 (for instance with the artificial horizon), an erected 3D representation is possible.

FIG. 8 illustrates a state of the image acquisition unit 130 that is rotated in relation to the orientation in FIG. 7. Accordingly, the (new) sensor horizon 220 is rotated by a certain angle 222 in relation to the previous sensor horizon 218. However, if the previous sensor horizon 218 is oriented parallel to the artificial horizon of position reference 166, this is no longer the case with the new sensor horizon 220. In addition to the rotated base 216, it is also clear that there is a height offset marked 226.

The rotation/inclination in FIG. 8 makes 3D display difficult, for instance when an image erection is desired, i.e. an "upright" represented image 164, also with a rotating image acquisition unit 130. This applies all the more to instruments 110 with an inclined direction of view (in relation to the longitudinal axis of the shaft 114, which is also the rolling axis, for example).

The present disclosure addresses these drawbacks with different modes of presentation. On the one hand—as far as it is possible—emphasis is put on the 3D representation. If, however, a 3D representation does not appear to be useful due to the given rotation position of the image acquisition unit, the observer is offered a 2D representation. In 2D mode, the (digital) image erection can be ensured. The 2D mode is suitable for applications, in which the orientation of the view from the observer's point of view is more important than stereoscopic observation in 3D mode.

In this context, reference is made to FIGS. 9-14. FIGS. 9-14 illustrate the currently selected rotation orientation of the observation instrument 110 with reference to an angular scale 230 by means of a position arrow 232. Furthermore, FIGS. 9-14 show the resulting representation and orientation for the reproduced image 164 of the object of observation with the display unit 160 in relation to a position reference 166 (e.g. an artificial horizon), provided that the image processing with the control device 150 is performed according to an exemplary embodiment of the present disclosure. It is understood that the representations of the tilt angles in FIGS. 9-14 are only of an exemplary nature. Larger, but also smaller ranges with 3D representation are conceivable.

The rotation angular scale 230 comprises different ranges 240, 242, 244, 246, of which the ranges 240 and 244 are exemplarily assigned to the first representation mode with 3D display. The ranges 242, 246 are associated with the second representation mode with 2D representation. The size of the respective ranges 240, 242, 244, 246 is exemplary. Between the ranges 240, 242, 244, 246 the transition between the different representation modes takes place at a switching angle.

The 0° position corresponds, for example, to the rotation angle state of the image acquisition unit 130 shown in FIG.

7. In the 0° position, the horizon 218, which is defined by the two sensors 180, 182 and/or the observation optics upstream thereof, corresponds to the artificial horizon (horizontal) of position reference 166. A 3D image of observation object 164 can thus be output. An image erection is not necessary insofar as the observation object 164 is displayed in the desired orientation even without additional measures.

If the instrument 110 and/or the image acquisition unit 130 is rotated, at small angles of rotation (see FIG. 10), it is still possible to stereoscopically reproduce the object of observation 164 (3D reproduction). Although there is no longer a perfect alignment between the horizon 218 and the position reference 166, the resulting deviation (see FIG. 8 for an example) is still acceptable with the rotation angle shown in FIG. 10. Accordingly, the observation object 164 can still be displayed stereoscopically.

In FIG. 10, the observation object 164 is displayed with a tilt angle in the range 240, which corresponds to the angle of the pointer 232 shown on the scale 230. This tilt, i.e. the image erection is omitted, is also still acceptable within certain limits. A potential advantage is that the 3D functionality is maintained, at least in certain embodiments. However, it is also conceivable to erect the observation object 164 shown in the image in the first representation mode (areas 240, 244), analogous to the orientation in FIG. 9. This would have the potential advantage of image erection, at least in certain embodiments. On the other hand, however, this could be accompanied by further impairments of the 3D representation. Within acceptable limits, this is nevertheless conceivable.

On the other hand, substantial exemplary embodiments take into account that the observation object 164 is at least in the range 240 not erected. This is also conceivable (regardless of the flip function that may be required) in the opposite range 244.

Between the representations in FIG. 10 and FIG. 11, there is a transition from range 240 to range 242. In other words, FIG. 10 shows the representation in the first representation mode (3D). FIG. 11 shows the representation in the second representation mode (2D). As already explained above, the electronic image erection is easier to implement in the second representation mode.

If the image of the object of observation 164 were to be erected abruptly at the rotation angle position indicated in FIG. 11 at the transition between the ranges 240, 242, there would be a noticeable "jump", comparable to the direct sequence of the representation of the object of observation 164 in FIG. 10 and the representation in FIG. 12, for instance. Instead, in the context of the present disclosure, it is proposed, at least in exemplary embodiments, to erect the image of the object of observation 164 smoothly and not abruptly, starting from the "orientation" transferred at the transition from the first representation mode to the second representation mode. Such a transitional movement makes the change between the two representation modes more convenient for the observer. In other words, an interpolation of the reproduced image between two orientations (partially rotated and erected) takes place.

Similarly, when switching from the second representation mode to the first representation mode, it is conceivable to correct the image erection in the 2D representation in order to anticipate a smooth transition to the expected tilting of the reproduced observation object 164 when entering the first representation mode. Here the image is interpolated between the erected orientation and the partially rotated orientation. See also the transition described further below in FIG. 13 and FIG. 14.

FIG. 12 illustrates that an image erection is then possible within range 242, in which the second representation mode is used. The image erection can be performed with the 2D image of the observation object 164 in a manner that is basically already known. The digital image erection is thus known. Furthermore, the image erection by moving the image sensor is known.

The pointer 232 is located in FIG. 12 at a limit angle in the range 242. In the exemplary embodiment, the limit angle is approximately 90°. In the opposite range 246, which is also assigned to the second representation mode, a further limit angle is approximately 270°. At least when the instrument is rotated towards the limit angle, i.e. by approximately 90° or 270°, the exemplary embodiment involves a complete image erection. At the limit angle, the observation object 164 is perfectly or at least approximately aligned in relation to the position reference. Between the orientation at the switching angle (transition between range 240 and range 242, see also FIG. 11) and the orientation at the limit angle according to FIG. 12, a gradual erection of the object of observation 164 dependent on the rotation angle can take place.

Based on the orientation in FIG. 12, FIG. 13 illustrates a state, in which the pointer 232 is still in the range 242 but is approaching the range 244. Thus, starting from the second representation mode, a transition to the first representation mode is upcoming. Therefore, in FIG. 13 the orientation of the displayed observation object 164 is already adapted to the expected orientation when entering the first representation mode.

FIG. 14 shows such a state. The instrument 110 and/or the image acquisition unit 130 is rotated by almost 180°. Nevertheless, a 3D display is now possible again. Furthermore, the reproduced observation object 164 is at least vertically aligned in relation to the original arrangement (FIG. 9). Based on the given orientation of the instrument and/or the image acquisition unit 130, a so-called image flip takes place in FIG. 14, comprising on the one hand a rotation of the individual images by 180° and on the other hand an exchange of the two channels.

Overall, even with a rolling movement of the instrument and/or the image acquisition unit, the observer obtains an easily graspable image with comprehensible orientation. The 3D representation can always be used if this seems possible under the given conditions. It can be switched automatically between 3D and 2D. Manual switching is also conceivable, at least as an additional option.

It is understood that the sequence of illustrations in FIG. 9 to FIG. 14 relates to an instrument with a straight direction of view. However, the above statements may also be transferred to instruments with oblique/inclined direction of view. It is understood that the field of view of instruments with inclined direction of view moves in such a way that when the instrument is rotating, various objects of observation appear in the field of view. However, with regard to orientation, the above explanations can be applied thereto. At least when other instruments (forceps, tweezers and the like) are used in addition to the observation instrument and appear at least partially in the field of view, there may be a benefit.

Using the schematically highly simplified representation of FIGS. 15 and 16, the above-mentioned image flip is described when the instrument 110 is rotated by 180°. In FIG. 15 and FIG. 16, the instrument 110 is in one of the ranges 240, 244, where a 3D representation is useful and desired. In FIG. 15, there is a state, which corresponds approximately to the state according to FIG. 9. Each of the two sensors 180, 182 acquires an image for the two channels 194, 196. The control device 150 comprises a block, which schematically couples the two channels 194, 196 to the output channels 200, 202. In the configuration according to FIG. 15, the acquired image of the two sensors 180, 182 already has the desired orientation. Accordingly, only the signal of the two sensors 180, 182 must be combined to enable a 3D representation for the reproduced observation object 164.

In contrast, the two sensors 180, 182 capture the image upside down according to the configuration in FIG. 16 due to the rotation of 180° that took place in the meantime. However, if the image data of both channels 194, 196 were simply rotated (compare blocks 250, 252), the first channel and the second channel would still be swapped. Therefore, in the exemplary embodiment according to FIG. 16 it is suggested to rotate the two (partial) images of the two sensors 180, 182 on the one hand to erect the respective single image. Furthermore, in this exemplary embodiment, the signal of the two channels 194, 196 is swapped (cross swap) during processing and forwarding to the output channels 200, 202, exemplified by block 254. In this way, the image flip (also called 180° flip) is implemented. In range 244, an approximately erected display in 3D mode is possible, even if the instrument 110 and/or the image acquisition unit 130 are rotated by 180°. Close to the 180° position, a 3D display is also desired.

It is to be understood that the blocks 250, 252, 254 may be functional blocks of the control device 150. The blocks 250, 252, 254 can be implemented in software and/or hardware. The blocks 250, 252, 254 can be designed as discrete blocks with a specific individual function or as universal function blocks.

The functionality of the instrument 110 illustrated in FIGS. 9-16 may be controlled by the control device 150 in an assigned mode of operation. In an exemplary embodiment, the instrument 110 with the control device 150 is also capable of other modes of operation.

A first mode of operation includes, for example, operating the Instrument 110 in a pure 2D mode, i.e. without stereoscopic representation, and without image erection. The reproduced image will therefore rotate analogous to the rotation of the instrument 110 and/or the image acquisition unit. A second operating mode includes, for example, operation of the Instrument 110 in a stereo mode with stereoscopic representation. This means that an image erection is omitted.

A third mode of operation involves operating the instrument 110 in 2D mode, continuously erecting in relation to a reference horizon. Ideally, therefore, the rotation orientation of the displayed image does not change when the instrument is rotated. For the sake of completeness, it should be noted that for inclined view instruments the image content (field of view) changes when the instrument is rotated. However, the displayed image maintains its rotation orientation. The fourth mode is the combined operation with stereo representation (first representation mode) and 2D representation (second representation mode), where at least in the second representation mode the image is at least partially erected.

With reference to FIG. 17, the transition between the first representation mode and the second representation mode as well as a conceivable image transformation (interpolation) in the second representation mode as a component of the image erection is illustrated with reference to an angular scale 330, which in principle corresponds to the angular scale 230 according to FIGS. 9-16. The angular scale 330 represents a full circle, which corresponds to a complete rotation around the roll axis. Sub ranges 340, 344 are provided, which are assigned to the first representation mode. Furthermore subareas 342, 346 are provided, which are assigned to the second representation mode. Switching angles 350, 352, 354, 356 are assigned to the respective transitions. The switching angles 350, 352, 354, 356 are for example at 45°, 135°, 225° and 315°. In an alternative exemplary embodiment not shown in FIG. 17, the switching angles 350, 352, 354, 356 are at 30°, 150°, 210° and 330°.

The pointer 360 indicates the rotation position of the instrument 110 and/or its image acquisition unit 130 when rotating in the first representation mode (ranges 340, 344) and in the second representation mode (ranges 342, 346). FIG. 17 further shows limit angles 362, 364 in the respective sub range 342, 346 of the second representation mode. By way of example, the limit angles 362, 364 are each located in the middle of the sub range 342, 346, so the limit angle 362 is at 90°. The limit angle 364 is at 270°, by way of example.

FIG. 17 also contains a corresponding diagram 370, which shows an unfolding of the angular scale 330. An axis 372 describes the current angle of rotation/roll angle of the instrument 110 and/or its image acquisition unit 130 and thus corresponds to the respective position of the pointer 360 during rotation. A further axis 374 describes a resulting tilt angle, i.e. a resulting rotation orientation of the displayed image.

In the exemplary embodiment shown in FIG. 17, sub ranges 340, 344 cover ranges of 0°+/−45° and 180°+/−45°. In these ranges, a stereo representation is conceivable, the instrument can be operated in the first representation mode. In the first representation mode, no extensive electronic image erection is provided. Accordingly, the tilt of the displayed image with respect to the position reference (artificial horizon) is proportional or even directly proportional to the rotation angle of the instrument 110 and/or its image acquisition unit 130. This is illustrated in diagram 370 by the line designated by 380, compare the sections between 0° and 45°, between 135° and 225°, and between 315° and 360°. Thus, if the instrument 110 is rotated by 30° with respect to the position reference, the reproduced image is also rotated by 30°.

In the section between 135° and 225°, the instrument 110 is substantially upside down in its rotational orientation, so that the reproduced image may be adjusted in analogy to the exemplary embodiment illustrated in FIG. 16 to allow a static quasi-erection. The image of the two observation channels is then also turned upside down so that the output image has at least approximately the desired orientation.

In the remaining subareas 342, 346, a 2D representation based on one observation channel is used, compare the sections between 45° and 135° and between 225° and 315°. In the second representation mode, an electronic image erection is possible. This allows an adjustment of the orientation and/or a decoupling of the orientation of the displayed image from the current rotation angle of the instrument. In exemplary embodiments, however, immediate and constant erection of the output image to an ideal orientation in the second representation mode is omitted. Such an ideal orientation corresponds, for example, to the 0° position on axis 374 in the diagram 370. Such a function would have the consequence that the image rotates abruptly immediately upon passing one of the switching angles 350, 352, 354, 356, in the exemplary embodiment by 45° in relation to the 0° deflection. This can be seen as a disadvantage, especially when operating near the respective switching angle 350, 352, 354, 356, in certain embodiments.

In order to counteract such "jumping" of the reproduced image, it is suggested to interpolate the orientation of the image in the second representation mode depending on the angle, so that on the one hand a sufficiently stable erection and good orientation in the image is possible, and on the other hand jumps in the rotation angle are minimized or avoided.

The curves 382, 384, 386 illustrate exemplary angular orientations of the displayed image depending on the real rotation orientation of the instrument 110 and/or the image acquisition unit 130 in the second representation mode. These curves/lines 382, 384, 386 are arranged in the subareas 342, 346 of the second representation mode. The curves 382, 384, 386 provide in the second representation mode a transition between the distant subareas 340, 344 of the first representation mode, especially without angular jump.

The curve 382 is substantially proportional and/or inversely proportional to the current rotation angle of the instrument 110. For example, in the diagram 370, a linear section extends between the 45° position at the switching angle 350 and the 135° position at the switching angle 352. As the rotation angle of the instrument 110 increases, the displayed image is rotated in opposite directions as the rotation angle increases. Similarly, in the exemplary embodiment between the switching angles 354 and 356, i.e. between 225° and 315°, the image is rotated in the opposite direction. A boundary condition in the exemplary embodiment according to FIG. 17 is the passing through the 0° position at the limiting angles 362, 364, i.e. at 90° and at 270° rotation position of the instrument. In this way, with the symmetrical design, for instance mirror-symmetrical design with respect to the vertical, of the angle ranges 340, 342, 344, 346, a complete erection of the displayed image approximately in the middle of the respective sub range 342, 346 of the second representation mode results.

The curve 384 is in principle based on the course of curve 382. The course of the curve 384, however, follows the goal of performing a complete erection of the image not only directly at the limit angles 362, 364 but also in their surroundings (in the example approximately +/−20°). This results in a range, in which the displayed image is sufficiently stable and is not or only insignificantly rotated. Nevertheless, the curve 384 contains ramps, which allow a smooth transition to the first representation mode.

The curve 386 is exemplarily designed as a spline (polynomial curve), wherein the basic course is based on curve 384. In this way, "kinks" can be avoided when passing along the curve.

It is understood that the curves 382, 384, 386 for the second representation mode can be combined with the curve 380 for the first representation mode to implement the desired behavior in the first and second representation mode.

With reference to FIG. 18, a schematic block diagram is used to illustrate an exemplary embodiment of a method for stereo observation, for instance a method for stereo observation with image erection, at least partial image erection.

The method includes a first step S10, which relates to the provision of an observation instrument with stereo functionality. The instrument may be a stereo endoscope or a stereo exoscope. The instrument is usually equipped with an image acquisition unit that can acquire first image data and second image data. For this purpose, the image acquisition unit may comprise a first sensor and a second sensor offset from the first. In this way two observation channels (right and left) are formed. In this way, the first image data and the second image data can be combined for stereo observation. However, this poses challenges to the desired image erection when the instrument is rotated so that the stereo base of the instrument changes from an (ideal) reference horizon.

This is followed by step S12, which includes position monitoring and/or detecting a rotation angle position (roll position) of the instrument and/or its image acquisition unit. The detected position and/or the detected rotation indicates whether the given orientation of the image acquisition unit a 3D representation without image erection appears useful, or whether a switch should be made to a 2D representation using only one of the two observation channels in order to use electronic image erection.

Depending on the detected rotation angle a step S14 may follow, in which a first representation mode is activated. The first representation mode comprises a 3D playback. Alternatively, a step S16 may follow, in which a second representation mode is activated. The second representation mode comprises a 2D representation.

Step S14 is followed by step S18, which comprises a representation using both observation channels (right and left) for 3D representation with depth impression. At least in exemplary embodiments of the method it is intended that the image of the object of observation is not continuously erected in the first representation mode. Thus, the displayed image rotates together with the rotation of the instrument. However, since the first representation mode is only usable in limited rotation angle ranges, the rough image orientation is still valid, so that an orientation in the image is possible. Nevertheless, the first representation mode has the potential advantage of stereo observation, at least in certain embodiments.

Usually the first representation mode also includes a state, in which the instrument and/or its image acquisition unit is rotated by approximately 180°. Then the stereo base (defined for example by the position and/or orientation of the apertures of the observation optics) is again parallel or nearly parallel to the reference horizon. However, in order that the displayed image is not upside down, a so-called 180° flip is performed. This includes, for example, a 180° rotation of the two channels and an exchange (right with left, and vice versa). In this way, a quasi-erection in the 180° rotated state may be implemented together with the 3D representation. However, there is no continuous, closely tracked image erection.

However, if the method according to step S16 is executed in the second representation mode, only one of the two observation channels is provided and/or used for the representation in the following step S20. In certain embodiments, this may have the advantage that the stereo basis no longer needs to be taken into account, since only a mono signal is prepared for outputting.

Accordingly, the image to be output may be digitally/electronically erected. The image erection is carried out in step S22. Depending on the angle of rotation position that is still detected, tracking and/or continuous image erection can now be provided. For the observer the general orientation of the image does not change or only within defined limits when the instrument is rotated.

The method concludes in step S24 with the representation of the image, in the exemplary embodiment either a 3D representation without immediate image erection, except for an upside down orientation of the instrument, or a 2D representation with image erection.

With reference to FIG. 19, a further block diagram is used to describe an exemplary embodiment of a method for stereo observation. In principle, the method may also be designed and referred to as a method for controlling an imaging system.

The method starts with a step S50, which relates to for example the activation of the imaging system. This is followed by a step S52, which relates to the detection of a current rotary position (roll position) of an instrument and/or its image acquisition unit. For this purpose, at least one sensor may be provided. In step S54, the detection allows a monitoring of the detected angle. In step S56, it is determined, in which of three (global) angle ranges the instrument and/or its image acquisition unit is currently positioned. Here, for example, a position in relation to a reference horizon is taken into account, wherein the stereo base can be used as an internal instrument reference.

Depending on the angular range, the instrument can subsequently be operated in a first representation mode (step S58), a second representation mode (step S60), or a third representation mode (step S62), which is also referred to as transition mode.

The step S58 aims at a 3D representation using both image channels. Step S60 aims at a 2D representation using only one image channel and, in certain embodiments, also at a continuous image erection. Step S62 aims at providing a transition between the first representation mode and the second representation mode.

The step S58 is followed by step S64, which includes image manipulations adapted to the first representation mode for 3D observation. Step S64, for example, includes a so-called 180° flip, which takes into account a 180° rotation of the instrument. When the instrument is rotated by approximately 180° with a stereo base, 3D observation is basically possible again. In order for the image to appear upright to the observer, image manipulations are necessary, which are performed in step S64. At least in an exemplary embodiment of the method, it is not intended in the first representation mode to digitally erect the image, apart from the possible 180° flip.

The step S60 is followed by step S66, which includes image manipulations adapted to the second representation mode. The image is provided for the 2D representation. At least in some exemplary embodiments this includes a continuous image erection so that the reproduced image appears upright for the observer even if the instrument is rotated. The image erection can have a static target, i.e. exactly one target orientation. However, image erection may also be performed dependent on the rotation angle, especially to avoid large jumps when switching between the first representation mode and the second representation mode.

The step S62 is followed by step S68, which includes image manipulations adapted to the transition mode. The main purpose of the transition mode is to provide a smooth transition between the first representation mode and the second representation mode. For example, the transition between the display of two slightly offset fields (stereo) in the first representation mode and the display of only one image (2D), i.e. the data of only one observation channel, in the second representation mode. It is conceivable to fade out or fade in one of the two fields in the stereo mode within a certain period of time (for example, defined number of frames) so that the other of the two fields becomes the dominant image. In this way, the transition between 2D and 3D is smoothed. In this way, jumpy changes between successive frames are avoided.

In step S68 an adjustment and/or modification of the erection is made so that the image changes smoothly between the different modes for the observer, wherein instead of a "jump" a gentle transformation/rotation based on interpolations is noticeable, which is perceived as more convenient when viewed.

In the subsequent step S70, a representation is made taking into account the respective mode. The monitoring (step S54) is performed continuously during operation of the instrument if a corresponding operating mode is selected. The transition mode S62 allows a visually convenient transition between the first representation mode according to step S58 and the second representation mode according to step S60.

Step S72 concludes the method and includes, for example, deactivation of the imaging system.

What is claimed is:

1. A medical stereo imaging system, comprising:
   an observation instrument that comprises an image acquisition unit that is configured to detect first image data and second image data, which can be combined for stereo observation,
   at least one position sensor that is configured to detect an orientation of a stereo base of the instrument in relation to a position reference, and
   image data processing software, which is stored on a non-transitory computer-readable storage medium, that when executed:
   is operable in a first representation mode and a second representation mode, depending on the orientation of the stereo base of the instrument,
   is operable to output an image signal for display, which, in the first representation mode, includes a stereo signal based on the first image data and the second image data from the instrument, and, in the second representation mode, includes a mono signal based on the first image data or the second image data from the instrument, and
   is operable to erect images that are output with the image signal in the second representation mode, depending on the orientation of the stereo base of the instrument.

2. The imaging system of claim 1,
   wherein the software is further adapted to orient output images in the second representation mode so that an orientation of the displayed output image in relation to a display horizon does not change or only changes within defined limits.

3. The imaging system of claim 1,
   wherein the software is further adapted in the first representation mode to output images to be output in a non-erected state, so that changes in the orientation of the output images are associated with changes in the orientation of the stereo base of the instrument.

4. The imaging system of claim 1,
   wherein the software is further operable in a first rotation angle range of the stereo base of the instrument in the first representation mode, and
   wherein the software is further operable in a second rotation angle range of the stereo base of the instrument in the second representation mode.

5. The imaging system of claim 4,
   wherein the first rotation angle range comprises two sections that are off-set from each other by 180°.

6. The imaging system of claim 5,
   wherein the software is adapted to swap a first image signal and second image signal, and to rotate the first image signal and the second image signal by 180°.

7. The imaging system of claim 4,
   wherein the second rotation angle range involves at least one position of the stereo base of the instrument that is rotated by 90° with respect to the position reference.

8. The imaging system of claim 4,
   wherein the first rotation angle range comprises, in terms of an angular scale, in which 0° indicates an ideal orientation of the stereo base of the instrument in relation to the position reference, a first section covering a range having a first limit between 310° and 350° and a second limit between 10° and 50°.

9. The imaging system of claim 1,
wherein the software is further operable to provide an adapted transition when switching between the first representation mode and the second representation mode,
wherein the transition comprises an adaptation between an orientation of the mono signal in the second representation mode and an orientation of the stereo signal in the first representation mode at a switching angle between the first representation mode and the second representation mode.

10. The imaging system of claim 1,
wherein the orientation detected by the at least one position sensor is a rotation angle, and
wherein the control device is configured in the second representation mode to orient output images dependent on the rotation angle.

11. The imaging system of claim 10,
wherein the software is operable to produce a low-skip or skip-free transition between the first representation mode and the second representation mode.

12. The imaging system of claim 10,
wherein the software interpolates in the second representation mode the output images dependent on the rotation angle between the non-erected state and the erected state.

13. The imaging system of claim 10,
wherein the software is configured to erect output images in the second representation mode between a switching angle, which is associated with the transition between the first representation mode and the second representation mode, and a limit angle or limit angle range of the stereo base of the instrument in the second representation mode.

14. The imaging system of claim 13,
wherein the switching angle, in terms of an angular scale, in which 0° indicates an ideal orientation of the stereo base of the instrument in relation to the position reference, is between 25° and 50°.

15. The imaging system of claim 13,
wherein the software is adapted to rotate output images in the second representation mode between the limit angle or limit angle range and a further switching angle such that the orientation of the displayed image is adapted to the further switching angle when the instrument is rotated towards the further switching angle.

16. The imaging system of claim 15,
wherein the further switching angle, in terms of an angular scale at which 0° describes an ideal orientation of the stereo base of the instrument in relation to the position reference, is between 130° and 155°, and
wherein the limit angle is 90°.

17. The imaging system of claim 1,
wherein the observation instrument is arranged as an instrument having an inclined direction of view.

18. The imaging system of claim 1,
wherein the observation instrument accommodates the image acquisition unit, and
wherein the image acquisition unit comprises a stereo image sensor or two individual sensors that are offset relative to one another.

19. A stereo observation method comprising:
providing an observation instrument comprising an image acquisition unit that detects first image data and second image data, which can be combined for stereo observation,
detecting an orientation of a stereo base of the instrument in relation to a position reference, and
operating the imaging system depending on the orientation of the stereo base of the instrument in a first representation mode or a second representation mode, comprising:
in the first representation mode, outputting an image signal that includes a stereo signal based on the first image data and the second image data from the instrument,
in the second representation mode, outputting an image signal that includes a mono signal from the instrument, and
erecting the output images depending on the detected orientation, at least in the second representation mode.

20. A non-transitory computer-readable storage medium including computer program instructions, which, when executed by a processor of an imaging system cause the imaging system to perform a method comprising:
detecting an orientation of a stereo base of an observation instrument in relation to a position reference, and
operating the imaging system depending on the orientation of the stereo base of the instrument in a first representation mode or a second representation mode, comprising:
in the first representation mode, outputting an image signal that includes a stereo signal based on the first image data and the second image data from the instrument,
in the second representation mode, outputting an image signal that includes a mono signal from the instrument, and
erecting the output images depending on the detected orientation, at least in the second representation mode.

21. A medical stereo imaging system, comprising:
an observation instrument comprising an image acquisition unit that is configured to detect first image data and second image data, which can be combined for stereo observation,
at least one position sensor that is configured to detect an orientation of a stereo base of the instrument in relation to a position reference, and
a data processor that is connected to the image acquisition unit and the at least one position sensor and that is configured to:
operate in a first representation mode and a second representation mode, depending on the orientation of the stereo base of the instrument,
output an image signal on a display, which, in the first representation mode, includes a stereo signal based on the first image data and the second image data from the instrument, and, in the second representation mode, includes a mono signal based on the first image data or the second image data from the instrument, and
erect images that are output with the image signal in the second representation mode, depending on the orientation of the stereo base of the instrument.

* * * * *